United States Patent [19]

Price et al.

[11] Patent Number: 5,606,164
[45] Date of Patent: Feb. 25, 1997

[54] METHOD AND APPARATUS FOR BIOLOGICAL FLUID ANALYTE CONCENTRATION MEASUREMENT USING GENERALIZED DISTANCE OUTLIER DETECTION

[75] Inventors: John F. Price, McCordsville; James R. Long, Fishers, both of Ind.

[73] Assignee: Boehringer Mannheim Corporation, Indianapolis, Ind.

[21] Appl. No.: 587,017

[22] Filed: Jan. 16, 1996

[51] Int. Cl.$^6$ .......................................... G01J 3/457
[52] U.S. Cl. ........................ 250/339.09; 250/339.07; 250/339.12
[58] Field of Search .................... 250/339.01, 339.06, 250/339.07, 339.09, 339.12; 364/413.07, 413.08, 413.09, 413.11

[56] References Cited

U.S. PATENT DOCUMENTS

| | | | |
|---|---|---|---|
| 4,660,151 | 4/1987 | Chipman et al. | 364/498 |
| 4,661,913 | 4/1987 | Wu et al. | 364/500 |
| 4,975,581 | 12/1990 | Robinson et al. | 250/339 |
| 5,047,323 | 9/1991 | Colman et al. | 435/714 |
| 5,121,338 | 6/1992 | Lodder | 364/498 |
| 5,199,439 | 4/1993 | Zimmerman et al. | 128/670 |
| 5,210,778 | 5/1993 | Massart | 378/53 |
| 5,252,489 | 10/1993 | Macri | 436/87 |
| 5,258,907 | 11/1993 | Macri | 364/413.01 |
| 5,308,982 | 5/1994 | Ivaldi et al. | 250/339.01 |
| 5,316,953 | 5/1994 | Macri | 436/87 |
| 5,324,667 | 6/1994 | Macri | 436/918 |
| 5,324,668 | 6/1994 | Macri | 436/518 |
| 5,348,002 | 9/1994 | Caro | 128/633 |
| 5,348,003 | 9/1994 | Caro | 128/633 |
| 5,355,880 | 10/1994 | Thomas et al. | 128/633 |
| 5,379,764 | 1/1995 | Barnes et al. | 128/633 |

OTHER PUBLICATIONS

S. Wold and M. Sjorstorm, article entitled SIMCA: A Method for Analyzing Chemical Data in Terms of Similarity and Analogy, in *Chemometrics: Theory and Application*, B. R. Kowalski, Ed., American Chemical Society, Washington, D.C. 242–282, (1977). No Month.

(List continued on next page.)

*Primary Examiner*—David P. Porta
*Assistant Examiner*—David Vernon Bruce
*Attorney, Agent, or Firm*—Locke Reynolds

[57] ABSTRACT

A method and apparatus for measuring the concentration of an analyte present in a biological fluid is disclosed. The method includes the steps of applying NIR radiation to calibration samples to produce calibration data, analyzing the calibration data to identify and remove outliers, constructing a calibration model, collecting and analyzing unknown samples to identify and remove outliers, and predicting analyte concentration of non-outliers from the calibration model. Analysis of the calibration data includes data pretreatment, data decomposition to remove redundant data, and identification and removal of outliers using generalized distances. The calibration model may utilize principal component regression, partial least squares, multiple linear regression, or artificial neural networks, and reduction using principal component analysis or partial least squares scores. Unknown sample data is analyzed using data pretreatment followed by projection into the calibration model space, and identification and removal of outliers, with prediction of analyte concentration using the calibration model. The apparatus includes a pump which circulates a sample through tubing to fill a flowcell. Light from a NIR source is synchronized with a detector, facilitating light and dark measurements, and passes through a monochrometer and the flowcell and strikes the detector, whereby radiation transmitted through the sample is measured. Measurement data is stored in a general purpose programmable computer also controlling the pump, the detector, synchronization, and the monochrometer. The computer includes a general purpose microprocessor configured with computer program code employing the steps of the method.

42 Claims, 17 Drawing Sheets

OTHER PUBLICATIONS

H. L. Mark and D. Tunnell, Qualitative Near–Infrared Reflectance Analysis Using Mahalanobis Distances, Analytical Chemistry 57, 1449–1456, (1985). No Month.

E. R. Malinowski, Theory of the Distribution of Error Eigenvalues Resulting from Principal Component Analysis with Application to Spectroscopic Data, Journal of Chemometrics, 1, 33–40, (1987). No Month.

D. M. Haaland and E. V. Thomas, Partial Least–Squares Methods for Spectral Analyses, 1, Relation to Other Quantitative Calibration Methods and the Extraction of Qualitative Information, Analytical Chemistry, 60, 1193–1202, (1988). No. Month.

N. K. Shah and P. J. Gemperline, Combination of the Mahalanobis Distance and Residual Variance Pattern Recognition Techniques for Classification of Near–Infrared Reflectance Spectra, Analaytical Chemistry, 62, 465–470, (1990). No Month.

| Succession Number | Insufficient Serum Spl. | Ref. Error | Air Bubble | Mahal. Dist. (1580nm–1848nm) | Mahal. Dist. (2030nm–2398nm) | Omitted from Data Set |
|---|---|---|---|---|---|---|
| 1 | | | | • | • | |
| 3 | | | | • | • | •• |
| 4 | | | | • | • | •• |
| 5 | | | | | | |
| 12 | | | | | | |
| 23 | | | • | | | • |
| 28 | | | | • | | •• |
| 35 | • | | | | | • |
| 38 | • | | | | | • |
| 42 | • | | | | | • |
| 43 | | • | | | | • |
| 44 | | | | • | • | •• |
| 51 | | | | | • | |
| 52 | | • | | | | • |
| 58 | • | | | | | • |
| 65 | | | | • | | |
| 66 | | | | • | • | •• |
| 67 | | | • | | | • |
| 83 | | | • | | | • |
| 84 | • | | | | | • |
| 91 | | | | • | | |
| 96 | • | | | | | • |
| 111 | | | | • | | |

Fig. 16

METHOD AND APPARATUS FOR BIOLOGICAL FLUID ANALYTE CONCENTRATION MEASUREMENT USING GENERALIZED DISTANCE OUTLIER DETECTION

CROSS-REFERENCE TO PROVISIONAL APPLICATION

Benefit of applicants' prior filed copending provisional application Ser. No. 60/001,950 is hereby claimed.

BACKGROUND OF THE INVENTION

Spectral analysis is widely used in identifying and quantitating analytes in a sample of a material. One form of spectral analysis measures the amount of electromagnetic radiation which is absorbed by a sample. For example, an infrared spectrophotometer directs a beam of infrared radiation towards a sample, and then measures the amount of radiation absorbed by the sample over a range of infrared wavelengths. An absorbance spectrum may then be plotted which depicts sample absorbance as a function of wavelength. The shape of the absorbance spectrum, including relative magnitudes and wavelengths of peak absorbances, serves as a characteristic 'fingerprint' of particular analytes in the sample.

The absorbance spectrum may furnish information useful in identifying analytes present in a sample. In addition, the absorbance spectrum can also be of use for quantitative analysis of the concentration of individual analytes in the sample. In many instances, the absorbance of an analyte in a sample is approximately proportional to the concentration of the analyte in the sample. In those cases where an absorbance spectrum represents the absorbance of a single analyte in a sample, the concentration of the analyte may be determined by comparing the absorbance of the sample to the absorbance of a reference sample at the same wavelengths, where the reference sample contains a known concentration of the analyte.

One fundamental goal of a near-infrared spectroscopic method for biological fluid analyte concentration measurements such as blood glucose levels is to collect high quality data. Although great care may be taken to ensure reliable measurements by consistent sample preparation and data acquisition, data generated by instrumentation and clinical reference testing, like all data, are susceptible to the inclusion of errors from a number of sources. In large sets of data, it is not uncommon to have a number of measurements that are extremely deviant from the expected distribution of measurements, commonly referred to as outliers. Whether outliers result from statistical errors or systematic errors, outlier detection identifies samples containing such errors with sufficient confidence that such samples can be considered unique with respect to the sampled population. Inclusion of a small number of outliers within a set of measurements can degrade or destroy a calibration model that would otherwise be obtained by the measurements.

Referring to the method and apparatus of the present invention, there are at least four potential sources of error in the chemometric analysis for biological fluid analyte measurements such as measurements of blood glucose levels.

A first source of error is related to sample preparation. Blood serum samples require a great deal of preparation before chemometric analysis. During this preparation, a number of factors can affect the sample. For example, the amount of time that blood samples are allowed to clot may affect sample continuity in terms of fibrinogen content. The level of clotting also impacts the quality of centrifugation and ultimately the decanting of serum from cells. Samples prepared for clinical assays determine the quality of the data used for reference and calibration, so that great care must be exercised with the samples since this data will ultimately define the limit of prediction abilities.

A second source of error may result from the spectral measurement process. For example, the use of a flowcell for sample containment during data acquisition is susceptible to problems such as bubbles in the optical path as well as dilution effects from reference saline solution carryover. These dilution effects are usually negligible, but bubbles in the optical path are not infrequent and have a severe impact on data quality. In addition, errors produced by mechanical or electronic problems occurring within the analysis instrumentation can have important effects on data quality.

A third source of error is also related to the reference tests. Errors due to out-of-specification instrumental controls and low sample volume during clinical assays have similar effects to errors related to sample preparation, described above.

A fourth source of error, and probably the most difficult to identify and control, relates to sources of the samples, that is, to the individuals providing the biological fluids. A sample taken from an individual may at first seem to be quite unique with respect to a previously sampled population, but may in fact be an ordinary sample when a larger sample population is considered, that is, a putative unique sample may be only an artifact of undersampling.

All of these errors, alone or in combination, can lead to a calculated value of biological fluid analyte concentration that is at great variance with respect to measurements from samples taken from the same individual at approximately the same time. These extremely deviant values, which can be orders of magnitude greater or less than a predicted mean value, are outliers that should be identified prior to constructing a model for predicting biological fluid analyte concentrations.

The removal of outliers from a data set can be accomplished in a qualitative and subjective sense by graphical inspection of plotted data in those cases when the dimensionality is low, that is, where the number of data points associated with each measurement is small. In those instances where the number of data points associated with each measurement is large, however, outlier detection may be more quickly and efficiently be accomplished by a number of automatable procedures such as residual analysis. However, such procedures are often subject to a number of errors, or at least subject to errors in interpretation, especially in the relatively high dimensional spaces that are typically associated with multifactorial chemometric analyses.

SUMMARY OF THE INVENTION

To ensure accurate and consistent results, chemometric applications for biological fluid analyte measurement, such as glucose concentration determination, require multiple measurements taken from a number of individual test subjects over a period of time. However, even with consistent sample preparation and data acquisition, natural variations in samples and unintended errors can diminish the accuracy of results. Further, these errors are magnified by the relatively small number of biological fluid samples that can economically be drawn and tested. Automated techniques for outlier detection are necessary to assess the suitability of all acquired samples during both research phase and in final uses. The quality of data during clinical studies will define calibration models and the direction of subsequent research thrusts dependent upon results. In an end use, visual inspection of acquired data may or may not be possible. Even if inspection of the data is possible, independent objective methods of determination are needed which are not susceptible to subjective biases.

In order to aid in the understanding of the present invention, it can be stated in essentially summary form that it is directed to a method and apparatus for measuring biological fluid analyte concentration using outlier identification and removal based on generalized distances. The present invention improves the accuracy of biological fluid analyte concentration determination by identifying outlier values, and identifying and removing outliers from data before formation of a calibration model.

The present invention provides a method and apparatus whereby the concentration of an analyte in a sample of a biological fluid may be investigated by spectral analysis of electromagnetic radiation applied to the sample, including collecting calibration data, analyzing the calibration data to identify and remove outliers using the calibration model, constructing a calibration model, collecting unknown sample data, analyzing the unknown sample data to identify and remove outliers, and predicting analyte concentration of non-outliers in the unknown sample data by using the calibration model.

The analysis of the calibration data set may include data pretreatment, data decomposition to remove redundant data, and identification and removal of outliers as having a low probability of class membership, using generalized distance methods.

The construction of a calibration model may utilize principal component regression, partial least squares, multiple linear regression, or artificial neural networks, whereby the calibration data set may be reduced to significant factors using principal component analysis or partial least squares scores, enabling calculation of regression coefficients and artificial neural network weights.

The unknown sample data may be analyzed using data pretreatment, followed by projection into the space defined by the calibration model, and identification and removal of outliers in the unknown sample data as having a low probability of class membership. The prediction of analyte concentration of an unknown sample may include projecting data from the unknown sample into the space defined by the calibration model, thereby enabling determination of the analyte concentration.

A first embodiment of the apparatus of the present invention includes a pump into which a sample is introduced, the pump acting to circulate the sample through tubing to fill a flowcell, with the pump capable of both stopped flow and continuous flow operation. A sample compartment housing containing the flowcell and a detector is temperature controlled by a temperature control unit. Light from relatively broad bandwidth near-infrared source is directed through a chopper wheel, and the chopper wheel is synchronized by a chopper synchronization unit with respect to the detector, facilitating the apparatus of the present invention to make both light and dark measurements to substantially eliminate electronic noise. Modulated light then passes through a monochrometer, allowing variance of the wavelength of radiation continuously over an appropriate range. The monochromatic light passes through the flowcell and strikes the detector, whereby the amount of light transmitted through the sample is measured. Measurement data is stored in a general purpose programmable computer having a general purpose microprocessor, available for further processing according to the present invention. In addition, the computer may also control operation of the pump, the temperature control unit, the chopper synchronization unit, the chopper wheel, and the monochrometer.

In a second embodiment of the apparatus of the present invention, light from the relatively broad bandwidth light source is directed through the chopper wheel, and thereafter modulated light is passed through a filter wheel, whereby discrete wavelengths of radiation may be selected and transmitted to the flowcell.

In a third embodiment of the apparatus the present invention, a plurality of narrow bandwidth near-infrared sources, such as a plurality of laser diodes, is provided to produce near-infrared radiation at a preselected plurality of wavelengths. Light from a selected narrow bandwidth near-infrared source may be pulsed by a driver in synchronization with the detector and directed into the flowcell 106. Synchronization of the selected narrow bandwidth near-infrared source and the detector permits the apparatus to make both light and dark measurements, thereby substantially eliminating significant electronic noise. Selection of each of the set of narrow bandwidth near-infrared sources for emission of light to be transmitted into the flowcell may be selected in a convenient order, for instance in order of increasing or decreasing wavelength, by configuring the computer to sequentially pulse each of the set of narrow bandwidth near-infrared sources.

In computer implementation of the method and apparatus of the present invention, variations in the intensity of transmitted light as a function of wavelength are converted into digital signals by the detector, with the magnitude of the digital signals determined by the intensity of the transmitted radiation at the wavelength assigned to that particular signal. Thereafter, the digital signals are placed in the memory of the computer for processing as will be described.

The steps of the method of the present invention includes as a first step collecting data to be used in constructing a calibration model. After the calibration data have been collected, data pretreatment may be performed in order to remove or compensate for spectral artifacts such as scattering (multiplicative) effects, baseline shifts, and instrumental noise. Pretreatment of the calibration data may be selected from the group of techniques including calculating nth order derivatives of spectral data, multiplicative scatter correction, n-point smoothing, mean centering, variance scaling, and the ratiometric method.

Once data pretreatment, if any, has been performed on the raw calibration data, a calibration model may be formed. As near-infrared spectral data variables are highly correlated, to reduce the level of redundant information present, near-infrared spectral calibration data may be formed into a n×p matrix representing n samples, each measured at p wavelengths. The n×p matrix may be decomposed by principal component analysis into a set of n,n-dimensional score vectors formed into a n×n score matrix, and a set of n,p-dimensional loading vectors formed into an n×p loading matrix. The score vectors are orthogonal and represent projections of the n spectral samples into the space defined by the loading vectors and the major sources of variation.

Principal component analysis generates a set of n eigenvectors and a set of n eigenvalues, $\lambda_1 \geq \lambda_2 \geq \ldots \geq \lambda_n$. The eigenvalues represent the variance explained by the associated eigenvectors and can be divided into two sets. The first q eigenvalues are primary eigenvalues, $\lambda_1 \geq \lambda_2 \geq \ldots \geq \lambda_q$, and account for the significant sources of variations within the data. The remaining n–q secondary (error) eigenvalues $\lambda_{q+1} \geq \lambda_{q+2} \geq \ldots \geq \lambda_q$ account for residual variance or measurement noise.

The number of primary eigenvalues q may be determined by an iterative method which compares the $q^{th}$ eigenvalue's variance to the variance of the pooled error eigenvalues via an F-test. Further, reduced eigenvalues may be utilized, which weight the eigenvalues by an amount proportional to the information explained by the associated eigenvectors. The q score values for each sample are used to represent the original data during outlier detection, with the original spectra projected into the n×q dimensioned principal component subspace defined by loading the matrix.

Outliers may be identified using generalized distances, such as Mahalanobis distance or Robust distance. A generalized distance between a sample and the centroid defined by a set of samples may be determined using the variance-covariance matrix of the set of samples. Where the true variance-covariance matrix and the true centroid of a complete set of samples are unknown, a subset of the complete set may be used to form an approximate variance-covariance matrix and an approximate centroid. Further, by using principal component scores to represent spectral data for each sample, independent variables maximizing the information content may be obtained, insuring an invertible approximate variance-covariance matrix. With respect to Mahalanobis distance, an approximate centroid may be determined as the centroid of a multivariate normal distribution of the set of calibration samples and an approximate variance-covariance matrix of the set of calibration samples, whereby an approximate Mahalanobis distances in units of standard deviations measured between the centroid and each calibration sample may be found. With respect to Robust distance, by utilizing a minimum volume ellipsoid estimator (MVE), robust estimates of an approximate variance-covariance matrix and an approximate centroid may be obtained. Alternatively, a projection algorithm may be used to determine the Robust distance for each calibration sample.

After determining generalized distances for the calibration samples, the probability of class membership may be determined by a number of techniques, including evaluation of a chi-squared distribution function or utilizing Hotelling's T-statistic. Outliers are identified as having relatively large generalized distance which results in a relatively low probability of class membership. Samples whose class membership can be rejected at a confidence level that is greater than approximately $3-5\sigma$ may be considered as outliers. Following identification, outliers in the calibration samples may be removed. The generalized distances of outliers removed from the calibration samples may be examined, to determine whether additional data pretreatment is necessary. In the event that a relatively large number of outliers have very large generalized distances, further pretreatment of the calibration data may be indicated. After such additional pretreatment, the calibration data may again be subjected to analysis. On the other hand, if relatively large numbers of outliers do not have very large generalized distances, then additional data pretreatment may not be appropriate.

A calibration model may then be constructed utilizing any of a number of techniques, including principal component regression (PCR), partial least squares (PLS), multiple linear regression (MLR), and artificial neural networks (ANN). The calibration model will seek to correlate a set of independent variables representing absorbance values of n samples each measured at p wavelengths, with a set of dependent or response variables representing the concentration of an analyte in each of the n samples, by using a p-dimensional regression coefficient vector. A calibration model determines regression coefficient vector and is used to predict the concentration of the analyte in other samples, given only the absorbances at the p wavelengths.

As noted, near-infrared spectral data variables are highly correlated and while careful selection of the measurement wavelengths may minimize singularity problems, the spectral regions of interest may suffer from severe overlap and a high number of wavelengths is needed to model a multi-component system. Data compression may be used to address problems with collinearity to determining regression coefficient vector, so that redundant data may be reduced down to significant factors. Principal component regression is one technique that incorporates a data compression method. The technique of partial least squares may also be used to address the problem of redundant data.

With respect to both principal component regression and partial least squares, a determination is made of the appropriate number of score vectors or factors to be included in a calibration model that adequately represents the calibration data. The goal of selecting optimal number of factors for regression is to obtain parsimonious models with robust predictive abilities. Including too few factors causes model performance to suffer due to inadequate information during calibration, while including too many factors may also degrade performance. Principal components are normally sorted into an order so that the amount of variation explained by each principal component monotonically decreases. Later ordered principal components associated with small eigenvalues may be considered as containing measurement noise. By utilizing only the first q factors and omitting remaining factors, a type of noise rejection may be incorporated within principal component regression. The number of principal component analysis or partial least squares scores or factors to use during the regression step may be determined using the standard error of prediction, a measure of the error associated with each set of predictions. By plotting standard error of prediction against the number of factors used in each of the respective sets of predictions, a piecewise continuous graphical representation may be obtained and utilized to determine the number of factors to retain. One criterion for factor selection is to determine the first local minimum. Another technique for factor selection uses an F-test to compare standard error of prediction from models using differing numbers of factors.

In certain instances, data being analyzed may not be amenable to being split into a calibration, training set and a validation, test set. The reason may be due to a limited number of available samples or that by splitting data into two sets, one or both of the resulting sets do not adequately represent the sample population. In such situations, the iterative technique of leave one out cross validation may be used where, during each iteration, a sample is excluded from the calibration set and is used as a test sample. Prediction models using factors determined from calibration samples are then used to make test sample predictions. The test sample is then returned to the calibration set and another sample is excluded. The same process is repeated until all samples have been excluded from the calibration set and predicted by models generated by the calibration samples. All predictions are accumulated to give a standard error of validation.

Subsequent to determining the number of significant factors, the data set for the calibration model may be reduced to significant factors, and regression coefficients for the calibration model may be determined.

After construction of the calibration model, the calibration model may be applied to data collected from samples where concentration of analytes of interest are unknown. The unknown sample data may be appropriately pretreated and then projected into the principal component space defined by the calibration model. Next, generalized distances for the unknown sample data set may be found, using, for instance, either Mahalanobis or Robust distance as utilized with respect to the calibration data, and the probability of class membership may be estimated using the techniques described above, including evaluation of a chi-squared distribution function or utilizing Hotelling's T-statistic. Outliers in the unknown sample data are then identified based upon rejecting class membership at a confidence level that is greater than approximately 3–5σ. As the final steps of the method of the present invention, in the event that an unknown sample is not an outlier, the sample is projected into the space defined by the calibration model, and a prediction of the concentration of the analyte made. On the other hand, if the unknown sample is an outlier, the unknown sample may be rejected and no prediction as to analyte concentration made, although if possible, remeasurement of the unknown sample may be made to verify that the sample is an outlier.

With respect to the apparatus of the present invention, the steps previously described with respect to the method of the present invention may be configured on the general purpose microprocessor of the computer by employing computer program code segments according to each of such steps.

As those skilled in the art will appreciate, the present invention is intended to encompass without limitation a range of embodiments that can be better understood with reference to the drawings and following detailed description of the preferred embodiments of the invention.

BRIEF DESCRIPTION OF THE DRAWINGS

FIG. 16 is a table representing a summary of outlier detection results for 111 blood glucose samples over the spectral ranges 1580 nm to 1848 nm and 2030 nm to 2398 nm utilizing the present invention, and indicating possible causes of sample error.

DESCRIPTION OF THE PREFERRED EMBODIMENTS

The following portion of the specification, taken in conjunction with the drawings, sets forth the preferred embodiments of the present invention. The embodiments of the invention disclosed herein are the best modes contemplated by the inventors for carrying out their invention in a commercial environment, although it should be understood that various modifications can be accomplished within the parameters of the present invention.

Figure 1:
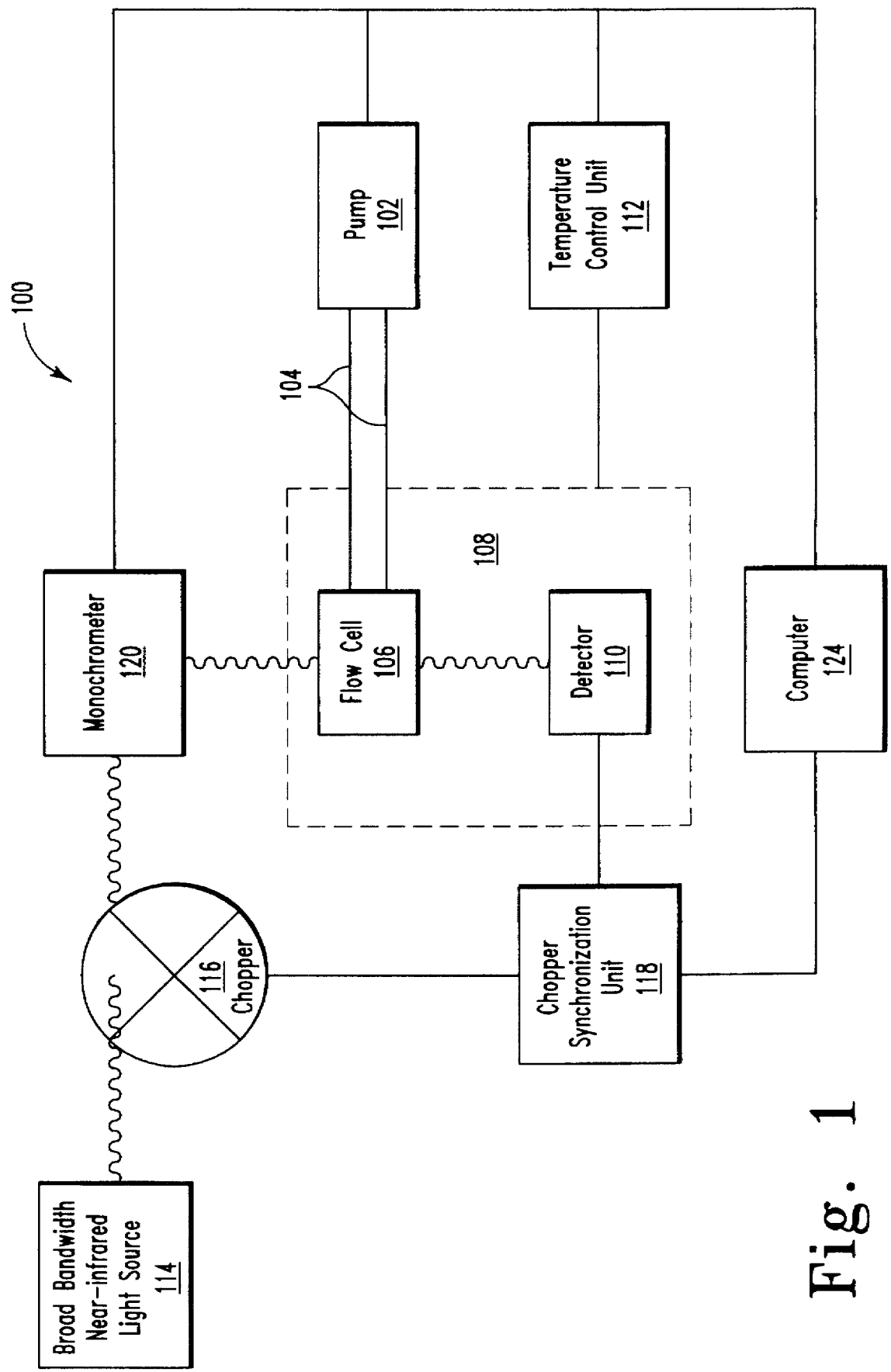
FIG. 1 is a schematic block diagram of a first preferred embodiment of the apparatus for biological fluid analyte concentration measurement representing the present invention.

Referring now to the drawings for a detailed description of the present invention, reference is first made to FIG. 1, depicting a first preferred embodiment of an apparatus for biological fluid analyte concentration measurement. In apparatus 100, a biological fluid sample may be introduced into pump 102 which circulates the sample through tubing 104 to fill flowcell 106. Pump 102 may be capable of both stopped flow and continuous flow operation. Sample compartment 108 contains flowcell 106 and detector 110, and is temperature controlled by temperature control unit 112. Light from relatively broad bandwidth near-infrared source 114 is directed through chopper wheel 116. Chopper wheel 116 is synchronized by chopper synchronization unit 118 with respect to detector 116, facilitating apparatus 100 to make both light and dark measurements to substantially eliminate electronic noise. Modulated light then passes through monochrometer 120, allowing continuous variance of the wavelength of radiation over an appropriate range. The monochromatic light passes through flowcell 106 and strikes detector 110. Detector 110 measures the amount of light transmitted through the sample. Measurement data is then stored in general purpose programmable computer 124 having a general purpose microprocessor, where the data will be available for further processing as will be described. In addition, computer 124 may also control operation of pump 102, temperature control unit 112, chopper synchronization unit 118, chopper wheel 116, and monochrometer 120.

Figure 2:
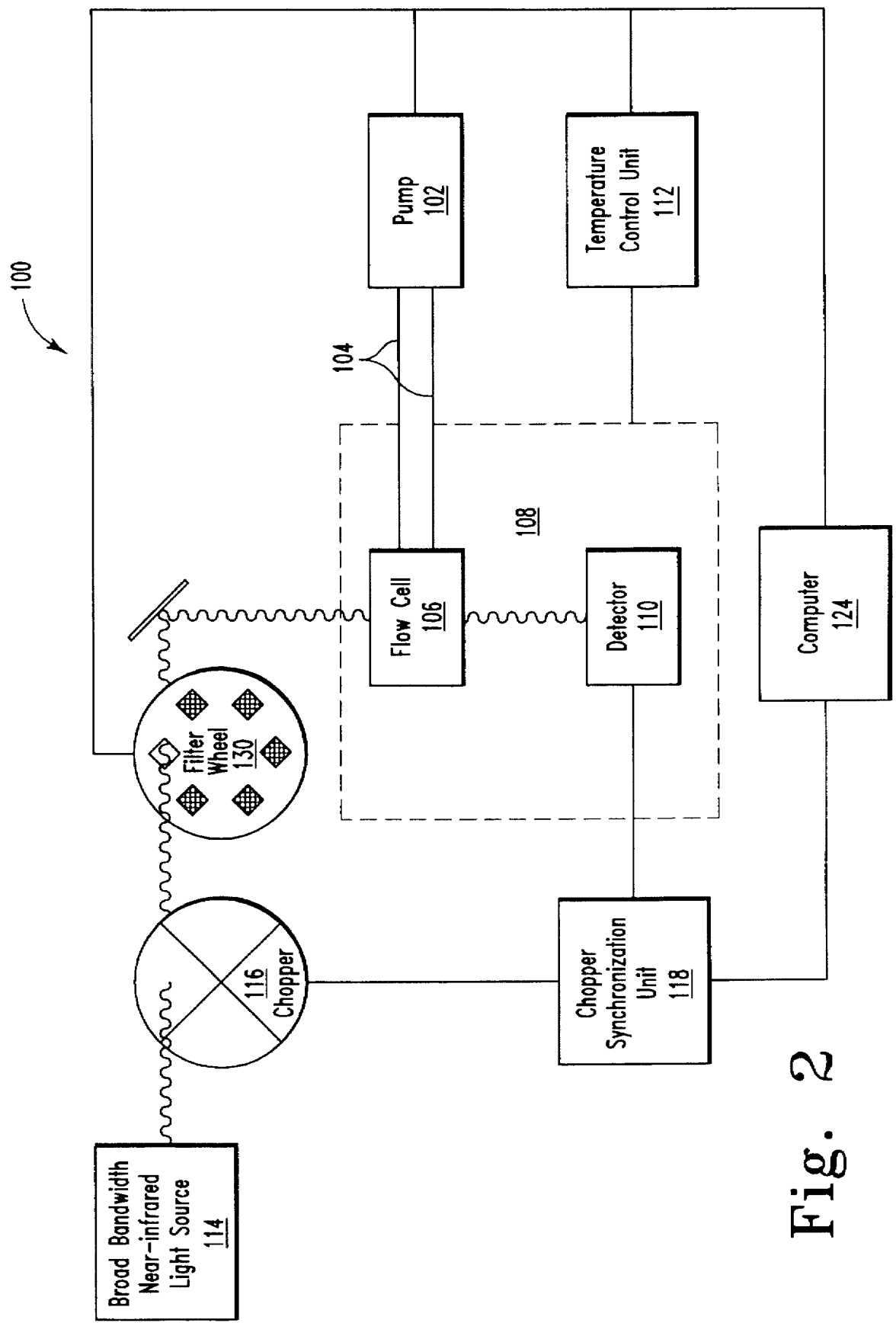
FIG. 2 is a schematic block diagram of a second preferred embodiment of the apparatus for biological fluid analyte concentration measurement representing the present invention.

In a second embodiment of apparatus 100 as depicted in FIG. 2, light from relatively broad bandwidth source 114 is directed through chopper wheel 116, and thereafter the modulated light is passed through filter wheel 130 whereby discrete wavelengths of radiation may be selected and transmitted to flowcell 106.

Figure 3:
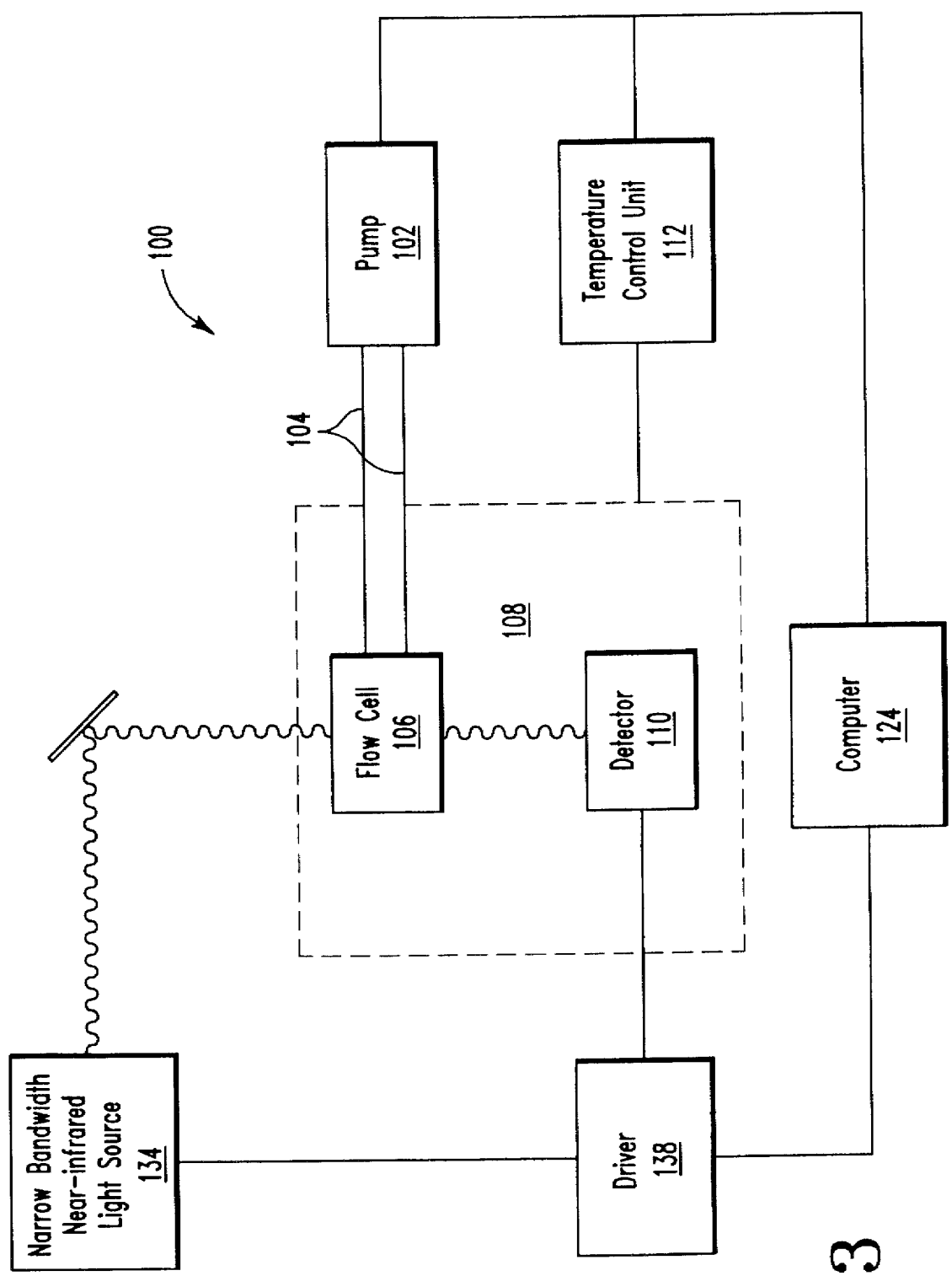
FIG. 3 is a schematic block diagram of a third preferred embodiment of the apparatus for biological fluid analyte concentration measurement representing the present invention.

In a third embodiment of apparatus 100 of the present invention as depicted in FIG. 3, a plurality of narrow bandwidth near-infrared sources 134, such as a plurality of laser diodes, is provided to produce near-infrared radiation at a preselected plurality of wavelengths. Light from a selected narrow bandwidth near-infrared source 134 may be pulsed by driver 138 in synchronization with detector 110 and directed into flowcell 106. Synchronization of the selected narrow bandwidth near-infrared source 134 and detector 110 permits apparatus 100 to make both light and dark measurements, thereby substantially eliminating electronic noise. Selection of each of the set of narrow bandwidth near-infrared sources 134 for emission of light to be transmitted into flowcell 106 may be selected in a convenient order, for instance in order of increasing or decreasing wavelength, by configuring computer 124 to sequentially pulse each of the set of narrow bandwidth near-infrared sources.

Referring to FIGS. 1–3, in computer implementation of the apparatus and method of the present invention, variations in the intensity of transmitted light as a function of wavelength are converted into digital signals by the detector, with the magnitude of the digital signals determined by the intensity of the transmitted radiation at the wavelength assigned to that particular signal. Thereafter, the digital signals are placed in the memory of computer 124, for processing as will be described.

Figure 4:
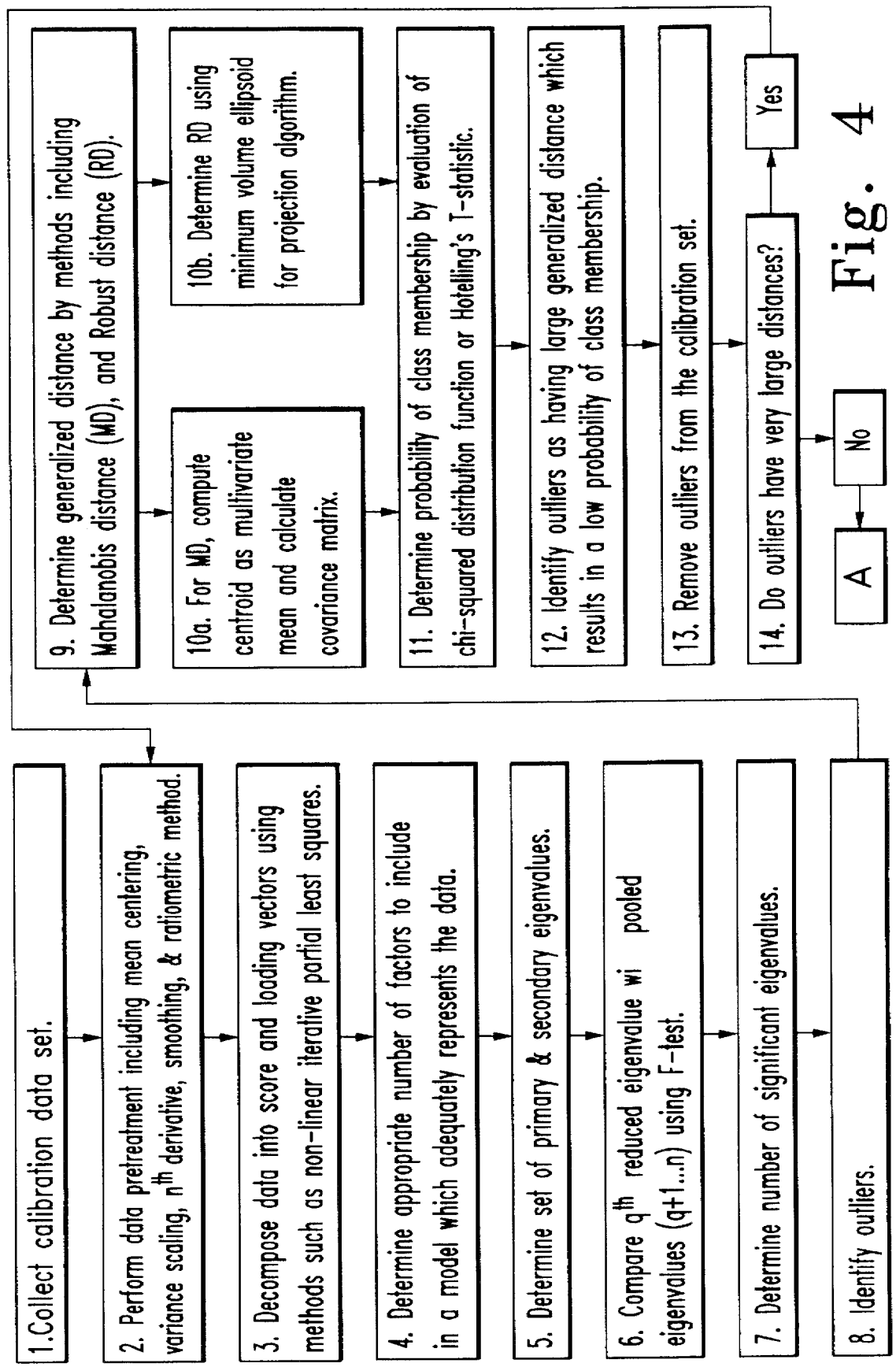
FIG. 4 is a flowchart representing initial steps of the method for biological fluid analyte concentration measurement representing the present invention.

As symbolically depicted in FIG. 4, step 1 in the method of the present invention refers to collecting data to be used in performing calibration and thereafter constructing a calibration model. After the calibration data have been collected, data pretreatment of step 2 may be performed, as it is often necessary to pretreat raw spectral data prior to data analysis or calibration model building in order to remove or compensate for spectral artifacts such as scattering (multiplicative) effects, baseline shifts, and instrumental noise. Pretreatment of the calibration data may be selected from the group of techniques including calculating nth order derivatives of spectral data, multiplicative scatter correction, n-point smoothing, mean centering, variance scaling, and the ratiometric method.

Once data pretreatment, if any, has been performed on the raw calibration data, steps directed towards forming a calibration model may be taken. With reference to step 3 as depicted in FIG. 4, near-infrared spectral data variables are highly correlated. To reduce the level of redundant information present, near-infrared spectral calibration data may be formed into a n×p matrix X representing n samples, each measured at p wavelengths, and may be decomposed by principal component analysis into a set of n,n-dimensional score vectors formed into a n×n score matrix T, and a set of n,p-dimensional loading vectors formed into an n×p loading matrix L, with $$X = TL^t. \tag{1}$$

In most spectroscopic applications, p>n, so that decomposition may be considered decomposing matrix X of rank n into a sum of n rank 1 matrices. The score vectors represent projections of the n spectral samples in X into the space defined by the loading vectors. The score matrix T represents the major sources of variation found within X, and the column vectors in T are orthogonal.

Referring to steps 4 and 5 as depicted in FIG. 4, principal component analysis generates a set of n eigenvectors and a set of n eigenvalues, $\lambda_1 \geq \lambda_2 \geq \ldots \geq \lambda_n$. The eigenvalues represent the variance explained by the associated eigenvectors. The eigenvalues may be divided into two sets. The first q eigenvalues are primary eigenvalues $\lambda_1 \geq \lambda_2 \geq \ldots \geq \lambda_q$ and account for the significant sources of variations within the data. The remaining n−q secondary, or error, eigenvalues $\lambda_{q+1} \geq \lambda_{q+2} \geq \ldots \geq \lambda_n$ account for residual variance or measurement noise.

With reference to steps 6 and 7 of FIG. 4, the number of primary eigenvalues q may be determined by an iterative method which compares the $q^{th}$ eigenvalue's variance to the variance of the pooled error eigenvalues via an F-test, $$F(1, n-q) = \frac{\lambda_q}{\sum_{j=q+1}^{n} \lambda_j} (n-q). \tag{2}$$

In addition, reduced eigenvalues which weight the eigenvalues by an amount proportional to the information explained by the associated eigenvectors may be utilized with the reduced eigenvalue is defined as $$\bar{\lambda}_q = \frac{\lambda_q}{(n-q+1)(p-q+1)}, \tag{3}$$

so that equation 2 may be expressed as $$F(1, n-q) = \frac{\sum_{j=q+1}^{n}(p-j+1)(n-j+1)}{(p-q+1)(n-q+1)} \cdot \frac{\bar{\lambda}_q}{\sum_{j=q+1}^{n} \bar{\lambda}_j}. \tag{4}$$

The $i^{th}$ sample in the principal component subspace is represented by the q score values of $t_i$. The q score values for each sample are used to represent the original data during outlier detection. In doing so, the original spectra are projected into the n×q dimensioned principal component subspace defined by loading matrix L.

As depicted symbolically in steps 8 and 9 of FIG. 4, outliers may be identified using generalized distances, such as Mahalanobis distance or Robust distance. A generalized distance between a centroid μ of a set of samples and the $i^{th}$ sample $x_i$ may be determined from $$D_i = [(x_i - \mu) \Sigma^{-1} (x_i - \mu)^t]^{1/2} \tag{5}$$

where Σ is the variance-covariance matrix of the set of samples. Where the true variance-covariance matrix and the true centroid of a complete set of samples are not determinable, a subset of the complete set of samples may be used to form an approximate variance-covariance matrix and an approximate centroid. In addition, by using principal component scores to represent spectral data for each sample, independent variables are orthogonal thus maximizing the information content and insuring an invertible approximate variance-covariance matrix.

Generalized distances may be Mahalanobis distances as described in step 10a of FIG. 4, with an approximate centroid $\bar{x}$ determined as the centroid of a multivariate normal distribution of the set of calibration samples and an approximate variance-covariance matrix of the set of calibration samples S. An approximate Mahalanobis distances $MD_i$ in units of standard deviations measured between the centroid and an $i^{th}$ calibration sample $x_i$ may thus be determined from $$MD_i = [(x_i - \bar{x})S^{-1}(x_i - \bar{x})^t]^{1/2} \quad (6)$$

where $$S = \frac{\sum_{i=1}^{q}(x_i - \bar{x})^t(x_i - \bar{x})}{(q-1)}. \quad (7)$$

With respect to Robust distance as depicted in step 10b of FIG. 4, by utilizing a minimum volume ellipsoid estimator (MVE), robust estimates of the approximate variance-covariance matrix $S_{Robust}$ and the approximate centroid $\bar{x}_{Robust}$ may be obtained, with Robust Distances $RD_i$ for the $i^{th}$ calibration sample determined from $$RD_i = [(x_i - \bar{x}_{Robust})S_{Robust}^{-1}(x_i - \bar{x}_{Robust})^t]^{1/2}. \quad (8)$$

Alternatively, a projection algorithm may be used to determine the Robust distance $RD_i$ for the $i^{th}$ calibration sample from $$RD_i = \max \left\{ \frac{|(x_i v_g^t - L(x_1 v_g^t, \ldots, x_n v_g^t)|}{Z(x_1 v_g^t, \ldots, x_n v_g^t)} \right\} \quad (9)$$

for g=1, . . . , n and where a scale of a minimum volume ellipsoid is given by $$Z(x_1 v_g^t, \ldots, x_n v_g^t) = \left(1 + \frac{15}{n-p}\right)(x_j v_g^t - x_{j-\frac{n}{2}} v_g^t) \quad (10)$$

and a location of a minimum volume ellipsoid is given by $$L(x_1 v_g^t, \ldots, x_n v_g^t) = \frac{(x_j v_g^t + x_{j-\frac{n}{2}} v_g^t)}{2}. \quad (11)$$

$x_i$ a p-dimensional vector representing the $i^{th}$ calibration sample, and $v_g$ is a p-dimensional vector representing the $g^{th}$ calibration sample defined by $$v_g = x_g - M \quad (12)$$

where M is a p-dimensional vector such that the $r^{th}$ component of M is given by the median of a set formed by the $r^{th}$ component of each of the n vectors $x_i$. For each value of g=1, . . . , n, index j used in equations 10 and 11 is determined from $$x_j v_g^t - x_{n/2+j} v_g^t = \min \{x_{n/2+1} v_g^t - x_1 v_g^t, x_{n/2+2} v_g^t - x_2 v_g^t, \ldots, x_n v_g^t - x_{n/2} v_g^t\} \quad (13)$$

where $x_1 v_g^t \leq x_2 v_g^t \leq x_3 v_g^t \leq \ldots \leq x_n v_g^t$.

After determining the generalized distances for the calibration samples, referring to step 11 shown in FIG. 4, the probability of class membership may be determined by a number of techniques, including evaluation of a chi-squared distribution function or utilizing Hotelling's T-statistic. As depicted in step 12, outliers are identified as having relatively large generalized distance which results in a relatively low probability of class membership. Generally speaking, samples whose class membership can be rejected at a confidence level in the range of approximately 3–5σ may be considered as outliers. Following identification, outliers in the calibration samples may be removed as depicted in step 13. Further, as indicated in step 14, the generalized distances of outliers removed from the calibration samples may be examined to determine whether additional data pretreatment is necessary. In the event that a relatively large number of outliers have very large generalized distances, further pretreatment of the calibration data may be indicated. If such further pretreatment of the calibration data is indicated, then after such pretreatment, the calibration data will again be subjected to the steps previously described beginning at step 2. On the other hand, if relatively large numbers of outliers do not have very large distances, then additional data pretreatment may not be appropriate.

Figure 5:
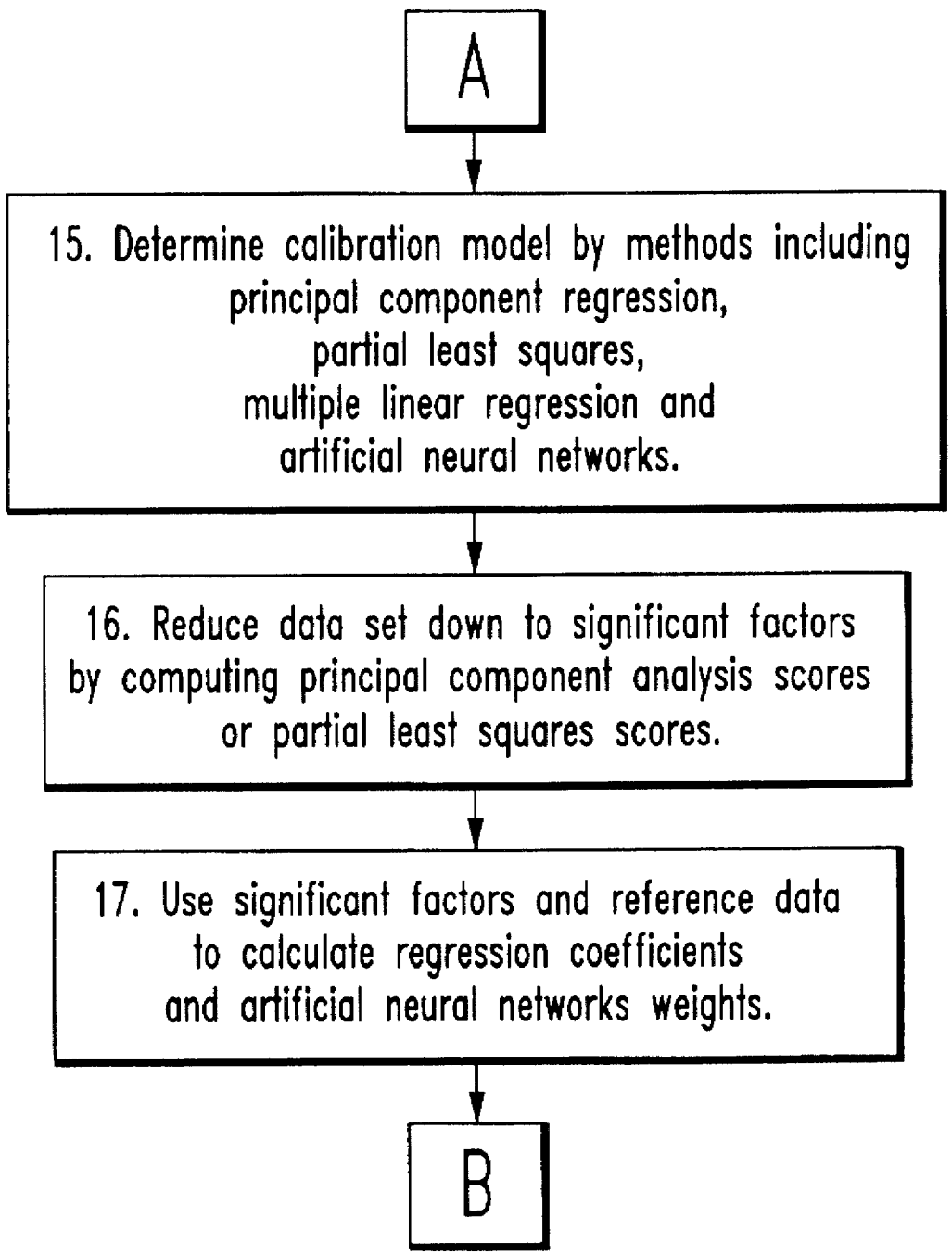
FIG. 5 is a flowchart representing intermediate steps of the method for biological fluid analyte concentration measurement representing the present invention.

Thereafter, as indicated by step 15 shown in FIG. 5, a calibration model may be constructed utilizing any of a number of techniques, including principal component regression (PCR), partial least squares (PLS), multiple linear regression (MLR), and artificial neural networks (ANN). The calibration model will seek to correlate a set of independent variables representing absorbance values of n samples measured at p wavelengths, symbolically represented by the n×p matrix X, with a set of dependent or response variables representing the concentration of an analyte in each of the n samples, symbolically represented by vector y. y is an n-dimensional vector, or alternatively, may be considered to be an n×1 matrix. After mean centering X and y, the relationship between X and y may be expressed as $$y = Xb + \epsilon \quad (14)$$

where b represents a p-dimensional regression coefficient vector (p×1) matrix) and s is an n-dimensional vector (n×1 matrix) representing errors in y. The calibration model determines vector b, using $$b = (X^t X)^{-1} X^t y. \quad (15)$$

Knowledge of b is used to predict the concentration of the analyte, y, in unknown samples, given only absorbances at each of the p wavelengths.

Referring to step 16, the determination of $(X^t X)^{-1}$ may be difficult as collinearity is inherent in spectroscopic data. As described, near-infrared spectral data variables are highly correlated. While careful selection of the measurement wavelengths may minimize singularity problems, the spectral regions of interest may suffer from severe overlap and a high number of wavelengths is needed to model a multicomponent system. Data compression may be used to address problems with collinearity to determining regression coefficient vector b, so that redundant data may be reduced down to significant factors.

Principal component regression is one technique to determine vector b that incorporates a data compression method. The first step in principal component regression is to perform principal component analysis on the calibration data as formed into matrix X. The score matrix T represents the major sources of variation found within X, and the column vectors in T are orthogonal. As a result, in the next step in principal component regression, T is used in place of X whereby an approximate value of b is found using $$b = (T'T)^{-1}T'y \quad (16)$$

as (TT') is invertible.

The techniques of partial least squares may also be used to address the problem of redundant data. One difference between partial least squares and principal component regression is the way in which the score matrix T and the loading matrix L are generated. As described, in principal component regression, using non-linear iterative partial least squares (NIPALS), loading vectors are extracted one at a time in the order of their contribution to the variance in X. As each loading vector is determined, it is removed from X and the next loading vector is determined. This process is repeated until n loadings have been determined. In partial least squares, concentration, y block, information is used during iterative decomposition of X. With concentration information incorporated into L, T values are related to concentration as well as placing useful predictive information into earlier factors as compared to principal component regression.

With respect to both principal component regression and partial least squares, determination must be made of the appropriate number of score vectors or factors to be included in a calibration model that adequately represents the calibration data. The goal of selecting optimal number of factors for regression is to obtain parsimonious models with robust predictive abilities. Including too few factors causes model performance to suffer due to inadequate information during calibration. Including too many factors may also degrade performance. Principal components are normally sorted into an order so that the amount of variation explained by each principal component monotonically decreases. Later ordered principal components associated with small eigenvalues may be considered as containing measurement noise. By utilizing only the first q factors and omitting the remaining factors, a type of noise rejection may be incorporated within principal component regression. The number of principal component analysis or partial least squares scores or factors, q, to use during the regression step may be determined as follows. In the case of matrix X with rank n,n preliminary calibration models are built. Each preliminary calibration model uses a different number of score vectors selected from the range of 1 through n score vectors. Predictions are then made form the n preliminary calibration models using the standard error of prediction technique. The standard error of prediction (SEP) is a measure of the error associated with each set of predictions and is given by $$SEP(k) = \sqrt{\frac{\sum_{i=1}^{n}(y_i - \hat{y}_{i,k})^2}{n-1}} \quad (17)$$

where the number of test set samples is given by n and $$\hat{y}_i = \bar{y} + (XL_r)b_r. \quad (18)$$

Figure 17:
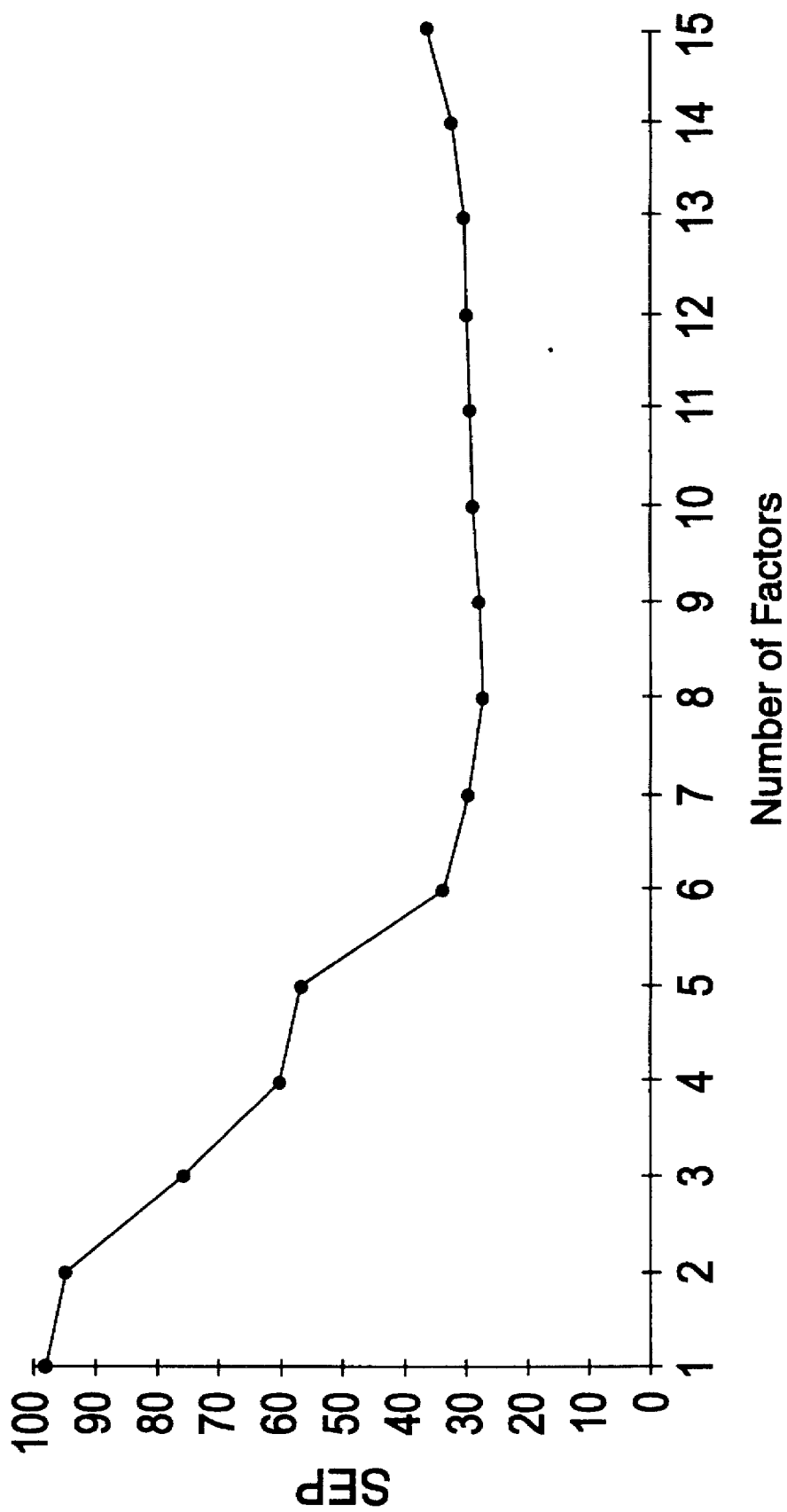
FIG. 17 is a graph of the standard error of prediction versus the numbers of factors used during regression.

By plotting standard error of prediction against the number of factors (score vectors) used, denoted by k, in each of the respective sets of predictions, a piecewise continuous graphical representation such as FIG. 17 may be obtained and utilized to determine the number of factors to retain. One criterion for factor selection is to determine the first local minimum. Applying a first local minimum criterion to the data graphed in FIG. 17, eight factors would be selected for the calibration model. A general interpretation of FIG. 17 is that significant information is being incorporated into the calibration model in factors one through six. As factors seven and eight are included, subtleties in the data are included. For factors nine through fifteen, variations or measurement noise specific to the calibration set are being modeled, so errors increase. Another technique for factor selection uses an F-test to compare standard error of prediction from models using differing numbers of factors. An F-test factor optimization would find that the standard error of prediction an eight factor model does not vary significantly from the standard error of prediction of a six factor model, whereby six factors is seen to be optimal.

In certain instances, data being analyzed may not be amenable to being split into a calibration, training set and a validation, test set. The reason may be due to a limited number of available samples or that by splitting data into two sets, one or both of the resulting sets do not adequately represent the sample population. The technique of leave one out cross validation may be used in such a situation. Leave one out cross validation is an iterative process, where during each iteration, a sample is excluded from the calibration set and is used as a test sample. Prediction models using 1 through n−1 factors determined from n−1 calibration samples are then used to make test sample predictions. The test sample is then returned to the calibration set and another sample is excluded. The same process is repeated until all n samples have been excluded from the calibration set and predicted by models generated by the n−1 calibration samples. All predictions are accumulated to give the standard error of validation (SEV) given by $$SEV(k) = \sqrt{\frac{\sum_{i=1}^{n}(y_i - \hat{y}_{(i),k})^2}{n-1}} \quad (19)$$

where the subscript (i) represents the $i^{th}$ leave one out iteration which leaves out the $i^{th}$ sample, with the standard error of validation then treated as standard error of prediction.

Referring to step 17, as depicted in FIG. 5, after determining the number of significant factors, data for the calibration model may be reduced to significant factors, and regression coefficients for the calibration model may be determined.

Figure 6:
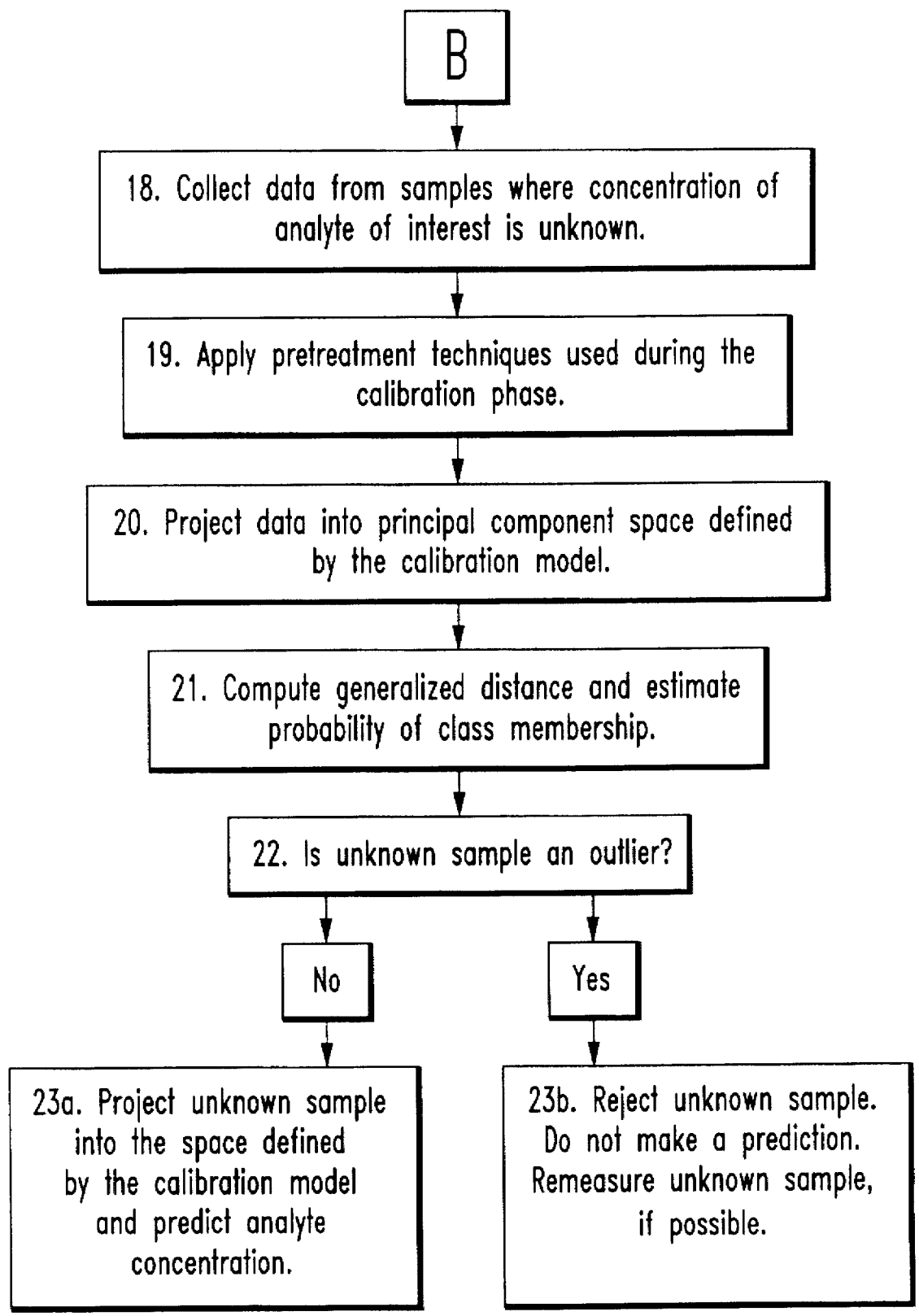
FIG. 6 is a flowchart representing final steps of the method for biological fluid analyte concentration measurement representing the present invention.

After construction, the calibration model as described above may be applied to data collected from samples where concentration of analytes of interest are unknown, symbolically indicated in FIG. 6 as step 18. The unknown sample data may be appropriately pretreated as indicated at step 19, with similar techniques to those described above with respect to pretreatment techniques capable of use with calibration data. Upon completion of pretreatment, the sample data may be projected into the principal component space that was previously defined by the calibration model, as indicated in step 20. In step 21, generalized distances for the unknown sample is found using the generalized distance, such as Mahalanobis or Robust: distances, that was utilized with respect to the calibration data; The probability of class membership may be estimated using the techniques described above, including evaluation of a chi-squared distribution function or utilizing Hotelling's T-statistic. Referring next to step 22, unknown sample outliers may then be identified based upon rejecting class membership at a confidence level that is in the approximate range of 3–5σ. In the event that an unknown sample is not an outlier, as in step 23a, the unknown sample may be projected into the space defined by the calibration model, and a prediction of the concentration of the analyte may be made. However, if the unknown sample is an outlier, as in step 23b, the unknown sample should be rejected and no prediction as to analyte concentration is made, although if possible, remeasurement of the unknown sample may be made for reanalysis to verify that the unknown sample is indeed an outlier.

With respect to the apparatus of the present invention, it will be understood that the steps previously described with respect to the method of the present invention may be configured on the general purpose microprocessor of computer 124 by employing computer program code segments according to each of such steps.

In use, the method and apparatus of the present invention was applied to blood glucose concentration data obtained from samples from 111 individuals. Six of the samples did not have enough serum to collect a near-infrared spectrum, so that vectors of zeros were used to fill their position within the data matrix in order to maintain succession number integrity during data manipulation. The six samples and the associated reference tests were omitted from future analyses. Two other samples were associated with reference test errors and were omitted, leaving 103 samples in the data set.

Figure 7:
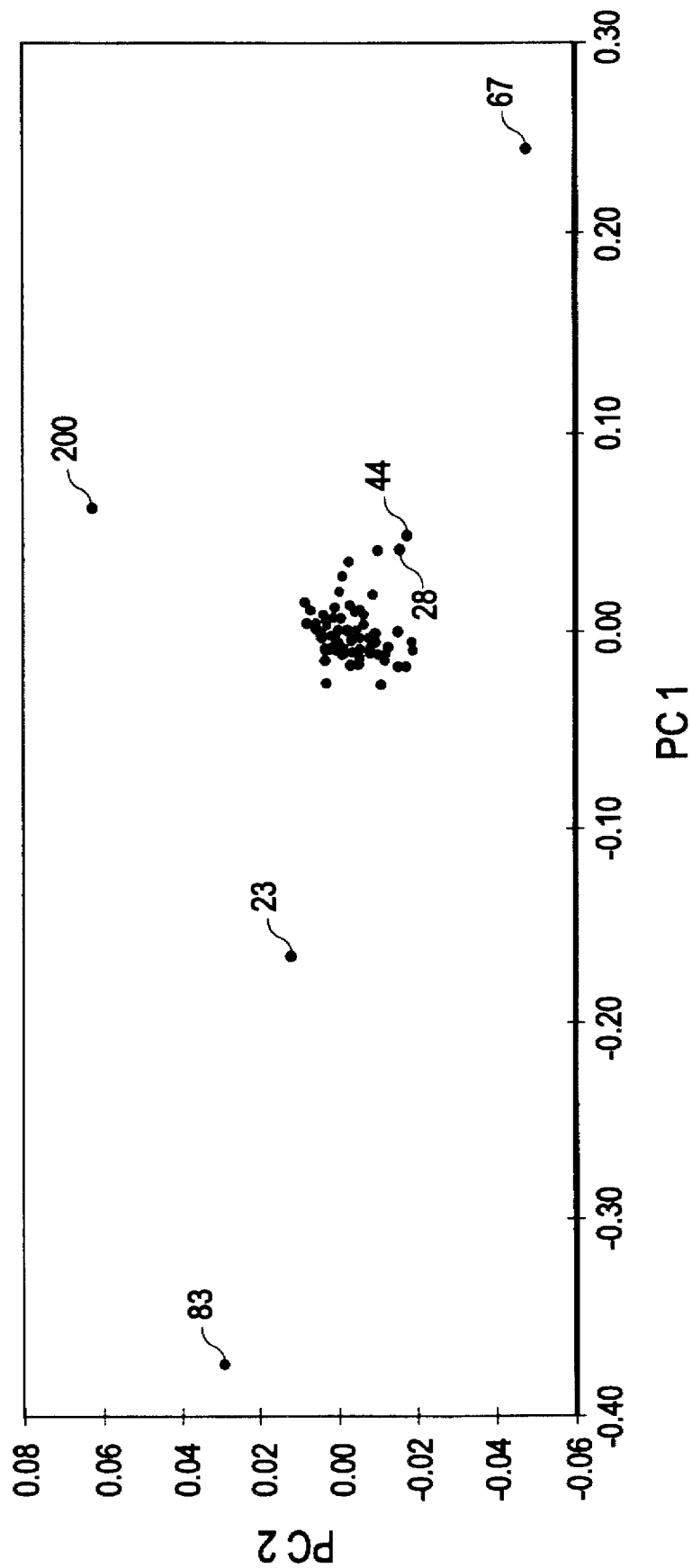
FIG. 7 is a scatter plot of principal component 2 versus principal component 1 of near-infrared spectra from 111 blood glucose samples in the range of 1580 nm to 1848 nm.
Figure 8:
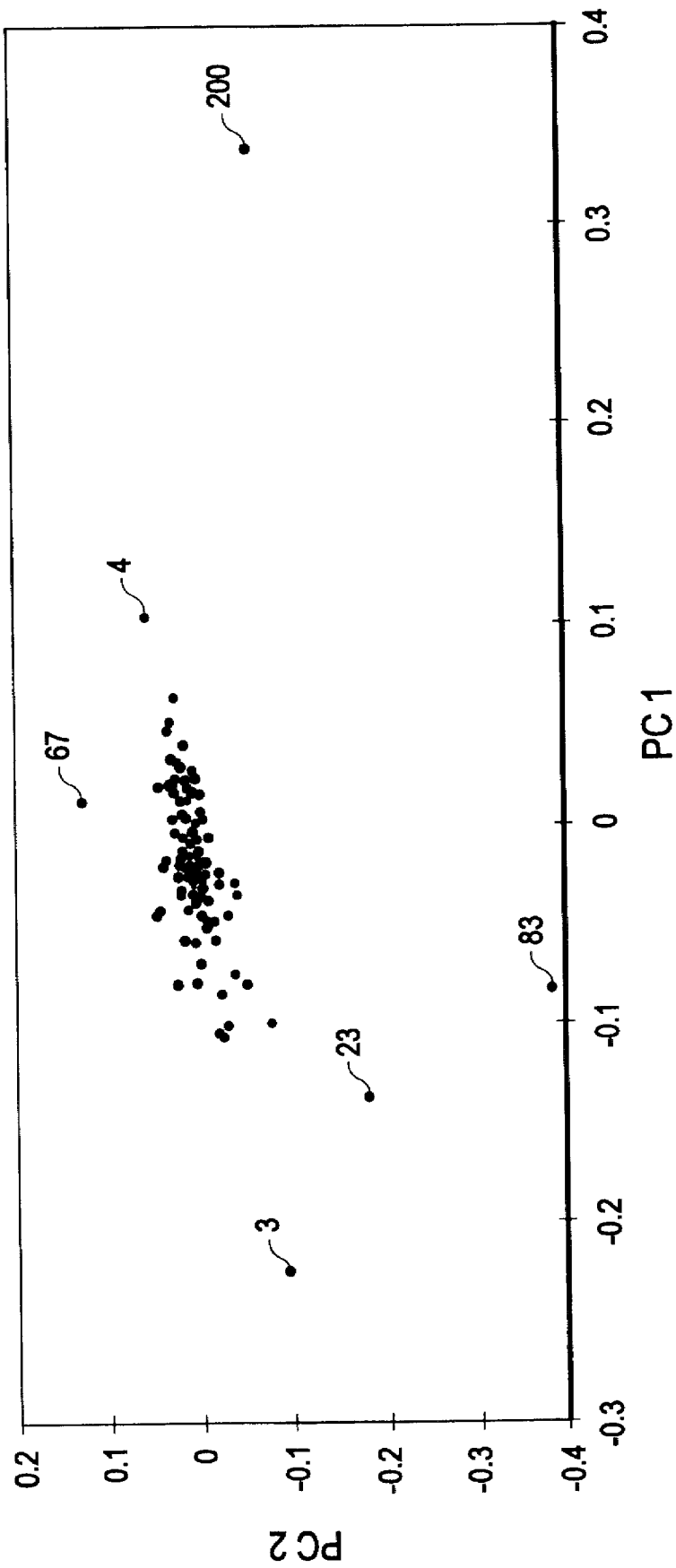
FIG. 8 is a scatter plot of principal component 2 versus principal component 1 of near-infrared spectra from 111 blood glucose samples in the range of 2030 nm to 2398 nm.
Figure 9:
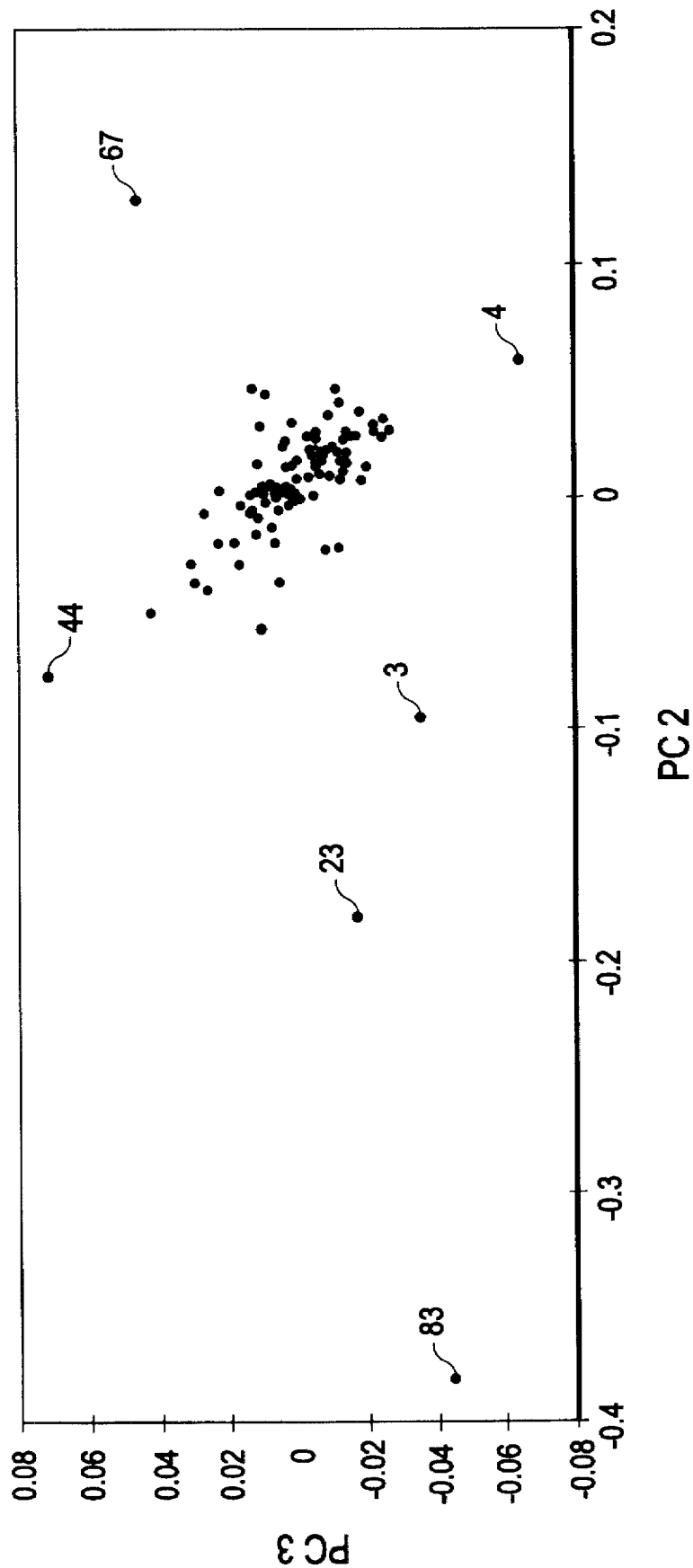
FIG. 9 is a scatter plot of principal component 3 versus principal component 2 of near-infrared spectra from 111 blood glucose samples in the range of 2030 nm to 2398 nm.

Potential outliers were identified through visual inspection of two dimensional and three dimensional scatter plots of principal component scores. FIGS. 7–9 depict separate principal component analyses of two spectral regions performed. Vectors of zeros, indicated by reference numeral 200, lie far from the main group of data, as expected. The near-infrared spectra of three samples, indicated by reference numerals 23, 67, and 83, each exhibited indications of interference due to bubbles in the optical path of the flowcell. As shown in FIGS. 7–9, such interference was present across the spectrum utilized as shown by distance of samples 23, 67, and 85 from the main group. In FIG. 7, samples 28 and 44 are seen to be potential outliers, as are samples 3 and 4 in FIG. 8. In FIG. 9, samples 3, 4, and 44 are potential outliers.

Figure 10:
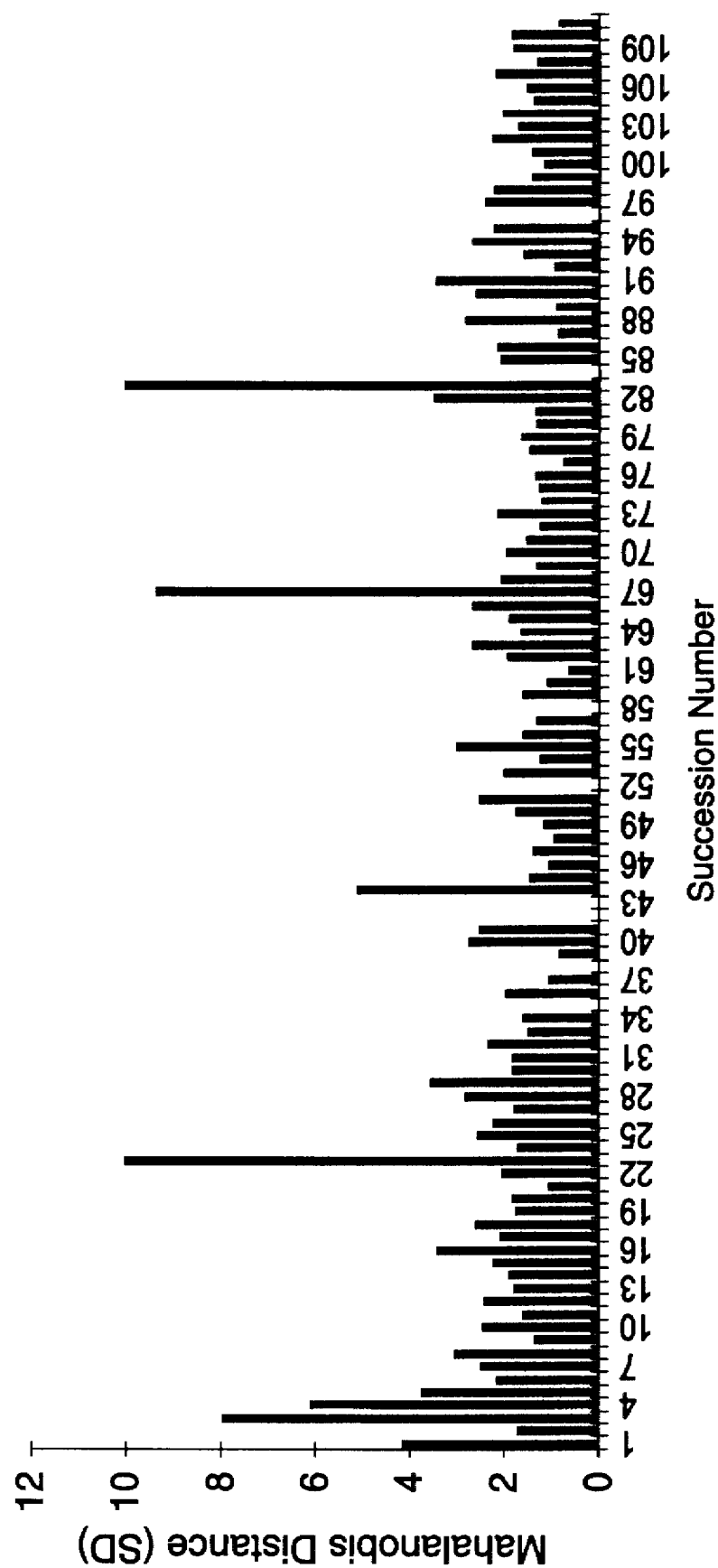
FIG. 10 is a bar graph of calculated Mahalanobis distances for 103 blood glucose samples in the range of 1100 nm to 2398 nm taken from data depicted in FIGS. 7–9.

Mahalanobis distances were calculated for the 103 samples, as shown in FIG. 10, wherein samples 23, 67, and 83 are seen to have Mahalanobis distances much greater than the other samples. Further, in FIGS. 10, 13, and 14, omitted samples are depicted as having zero Mahalanobis distance. A number of additional samples appear in FIG. 10 to be outlier candidates, including samples 3, 4, and 44. The data were subjected to further analyses, as will be described, with samples 23, 67, and 83 omitted, leaving 100 samples in the data set.

Figure 11:
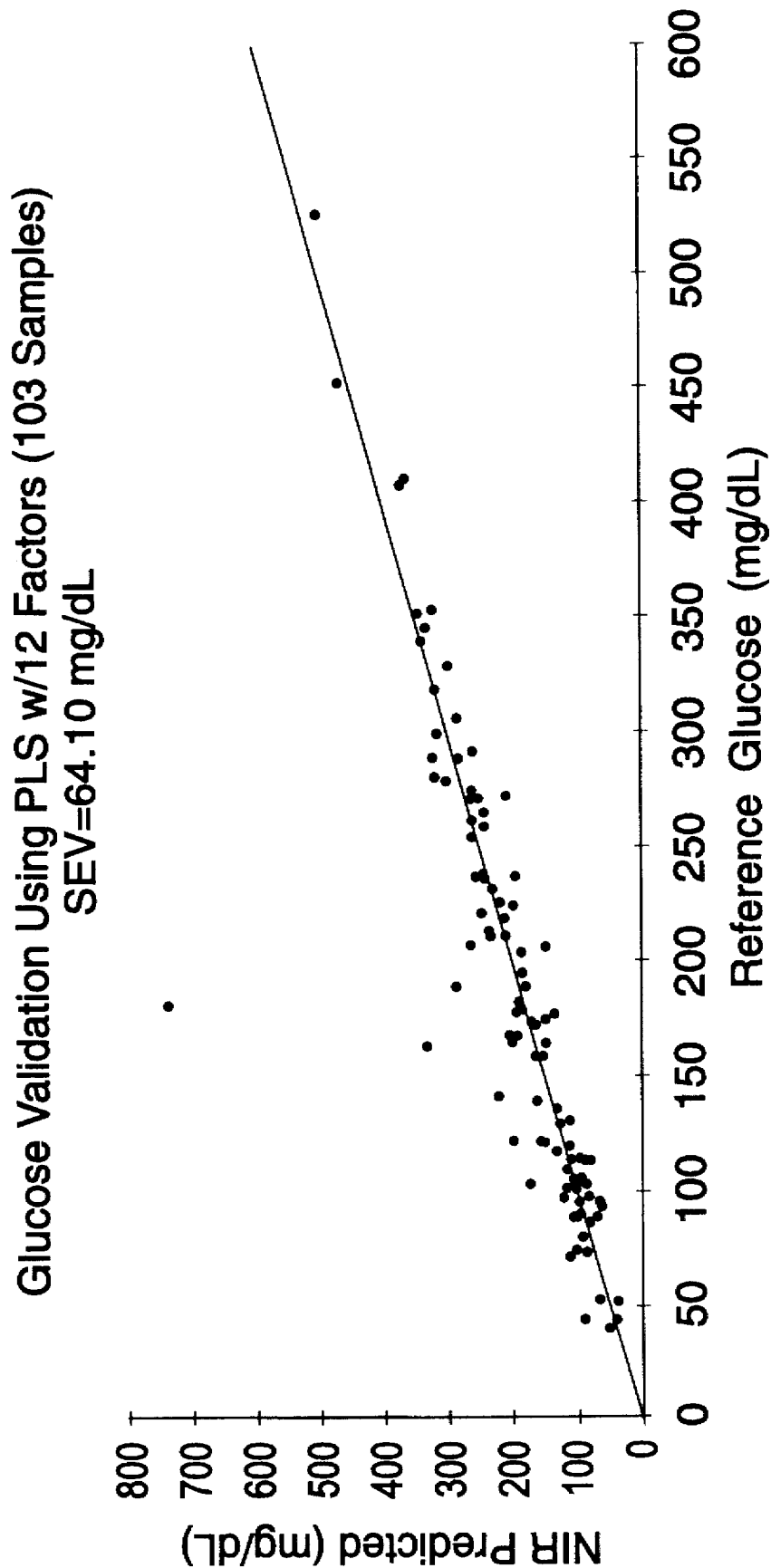
FIG. 11 is a scatter plot of predicted blood glucose concentrations from 103 samples using data derived from 2030 nm to 2398 nm, generated from a partial least squares model optimized with twelve factors attaining a standard error of validation of 64.10 mg/dL versus actual blood glucose concentrations.
Figure 12:
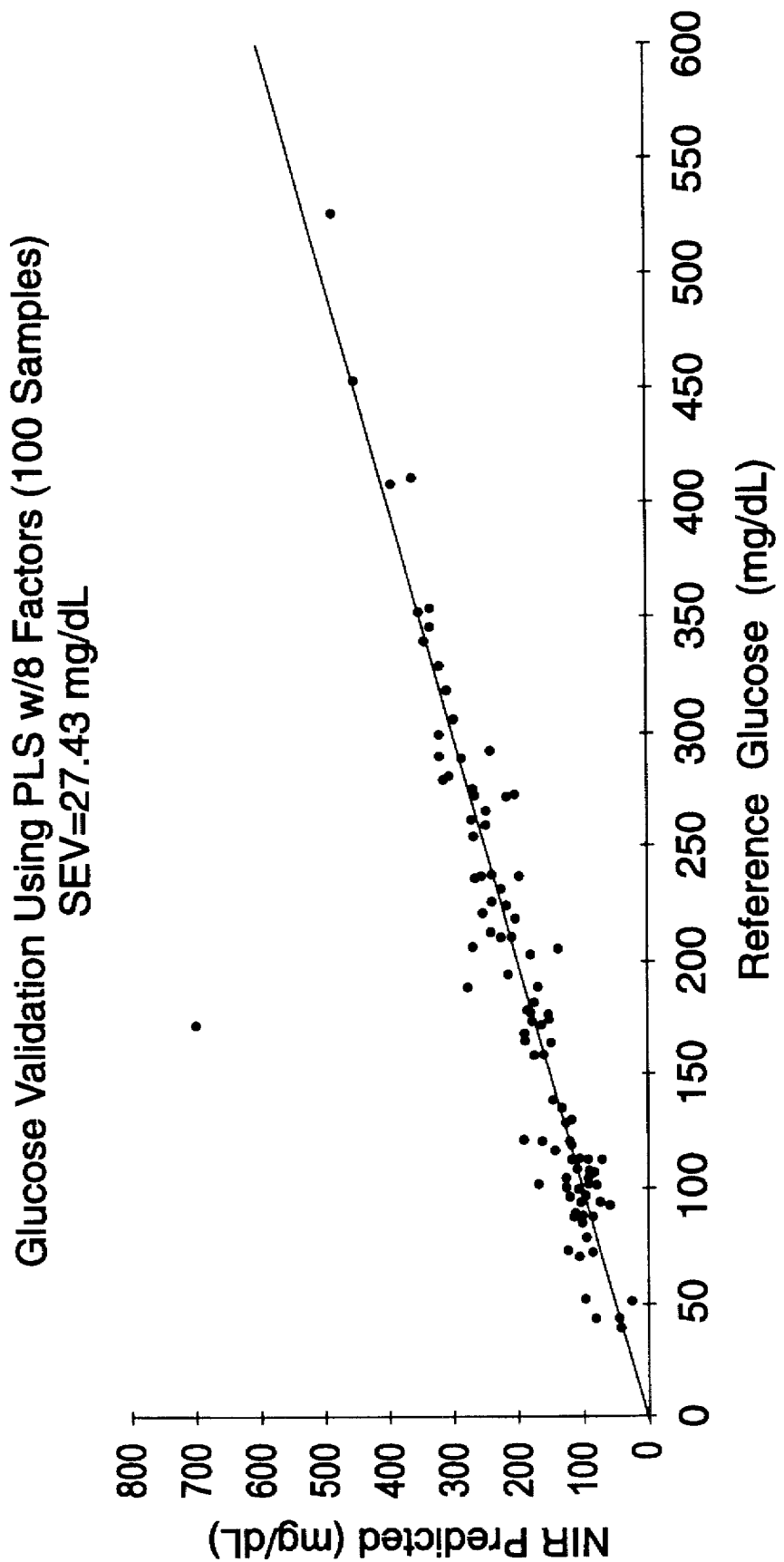
FIG. 12 is a scatter plot of predicted blood glucose concentrations from 100 samples using data derived from 2030 nm to 2398 nm, generated from a partial least squares model optimized with eight factors attaining a standard error of validation of 27.43 mg/dL versus actual blood glucose concentrations.

The detrimental impact of including outlier samples in a data set is illustrated in FIGS. 11 and 12. FIG. 11 depicts a scatter plot of predicted blood glucose concentrations from 103 samples using data derived from 2030 nm to 2398 nm generated from a partial least squares model optimized with twelve factors attaining a standard error of validation of 64.10 mg/dL versus actual blood glucose concentrations. With samples 23, 67, and 83 removed, FIG. 12 depicts a scatter plot of predicted blood glucose concentrations from 100 samples using data derived from 2030 nm to 2398 nm, generated from a partial least squares model optimized with eight factors attaining a standard error of validation of 27.43 mg/dL versus actual blood glucose concentrations. With gross outliers eliminated, the partial least squares technique utilized in the method of the present invention was able to make better predictions and use a less complex model, that is, a model using fewer factors. The sample depicted in FIG. 11 having a predicted value of approximately 750 mg/dL corresponded to sample indicated by reference numeral 83.

If sample 83 in FIG. 11 is ignored and the remaining samples in FIG. 11 are compared with those in FIG. 12, it is apparent that there is a wider spread of data about the identity line in FIG. 11. These results illustrate the influence of a relatively small number of outliers in seriously degrading the overall performance of a calibration model.

Figure 13:
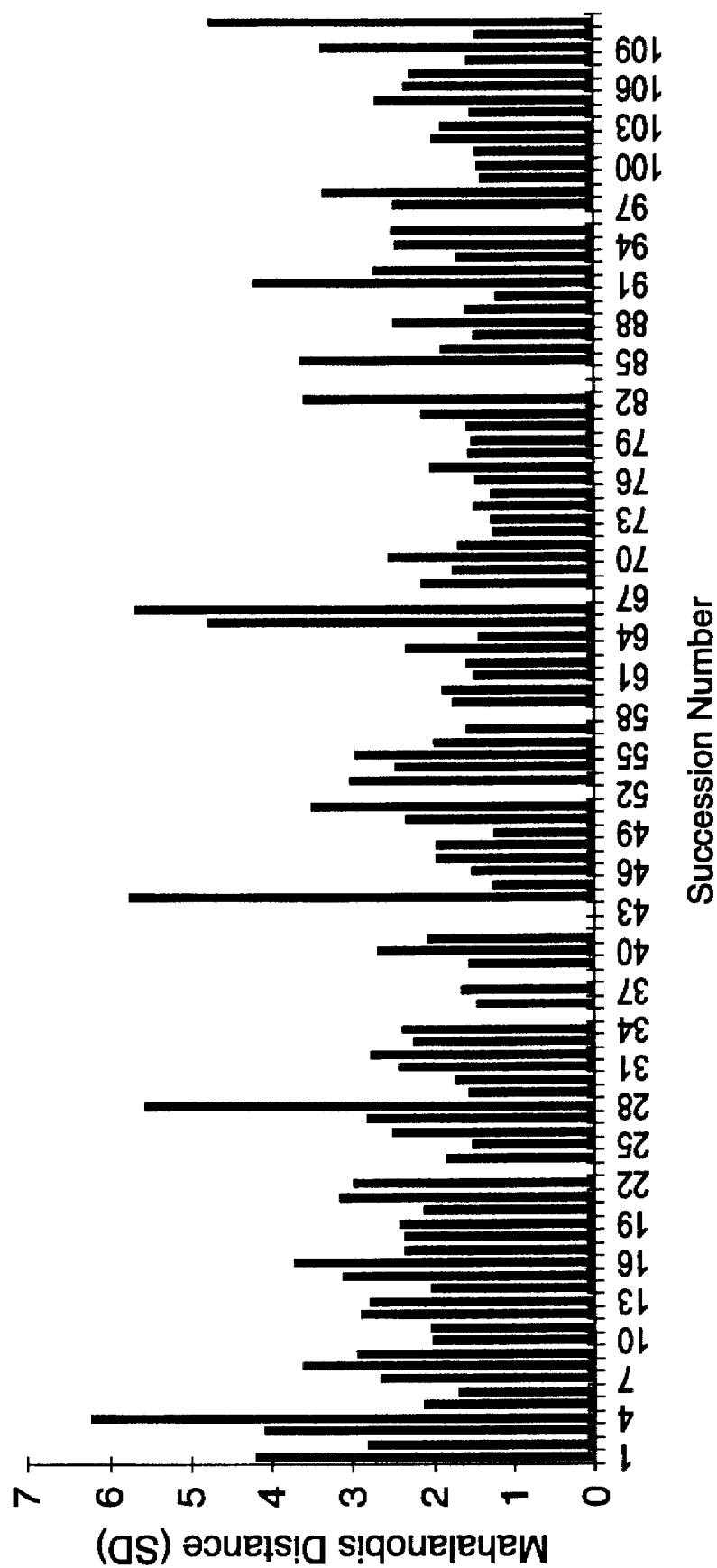
FIG. 13 is a bar graph of calculated Mahalanobis distances for 100 blood glucose samples in the range of 1580 nm to 1848 nm taken from data depicted in FIGS. 7–9.
Figure 14:
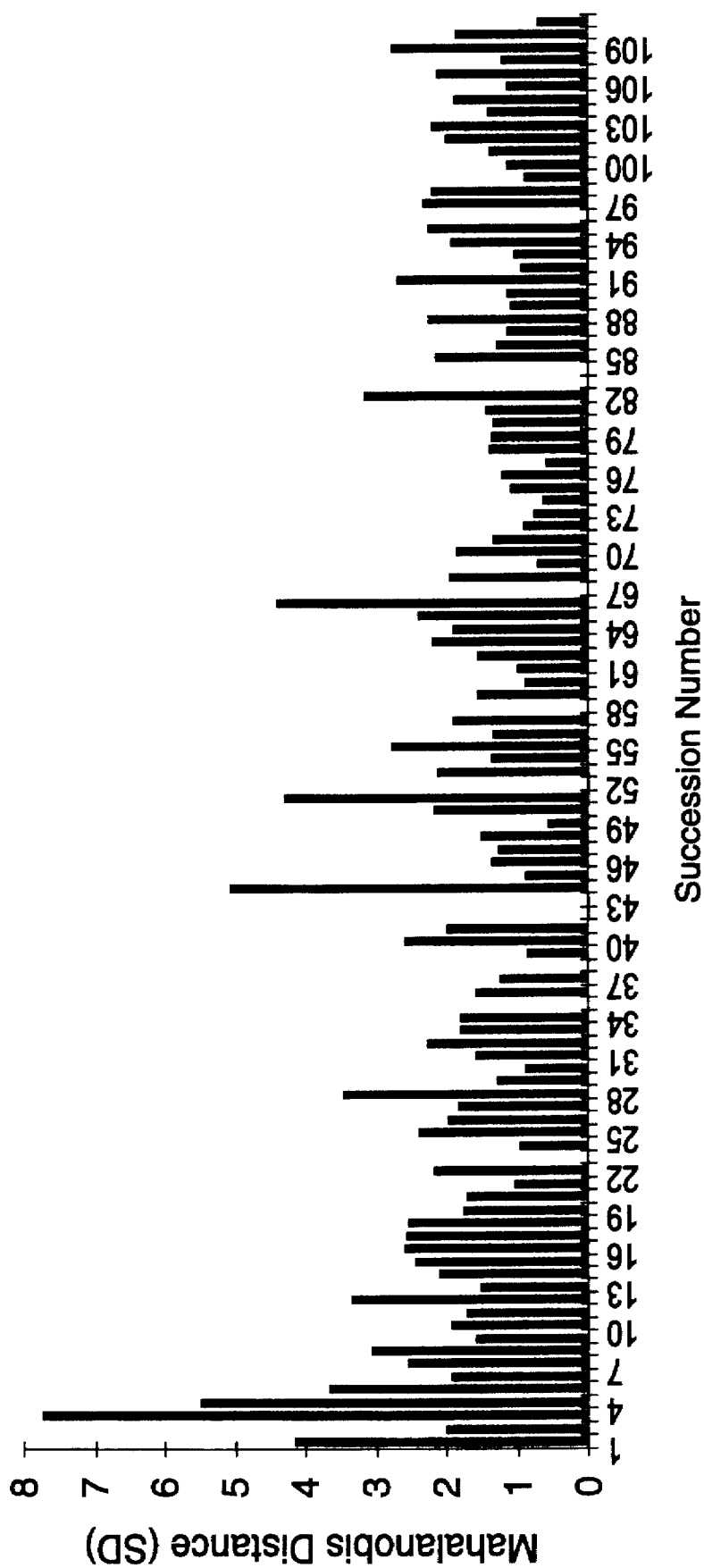
FIG. 14 is a bar graph of calculated Mahalanobis distances for 100 blood glucose samples in the range of 2030 nm to 2398 nm taken from data depicted in FIGS. 7–9.

Two spectral regions of the 100 samples were tested separately for outliers, with Mahalanobis distances for each of the regions shown in FIGS. 13 and 14. Nine samples were flagged as possible outliers in the 1580 nm to 1848 nm region, and six samples were flagged in the 2030 nm to 2398 nm region as possible outliers. As is apparent from comparison of FIGS. 13 and 14, the flagged samples were different in the two spectral regions. Outliers may be selected to be those flagged samples that are excluded from class membership in either or both spectral ranges, at a confidence level selected to be in the range of 3–5$\sigma$. Four of the samples rejected were also identified as possible outliers from the principal component score plots, FIGS. 7–9. Identification of the fifth sample required examination in the higher dimensional space associated with Mahalanobis distances.

Figure 15:
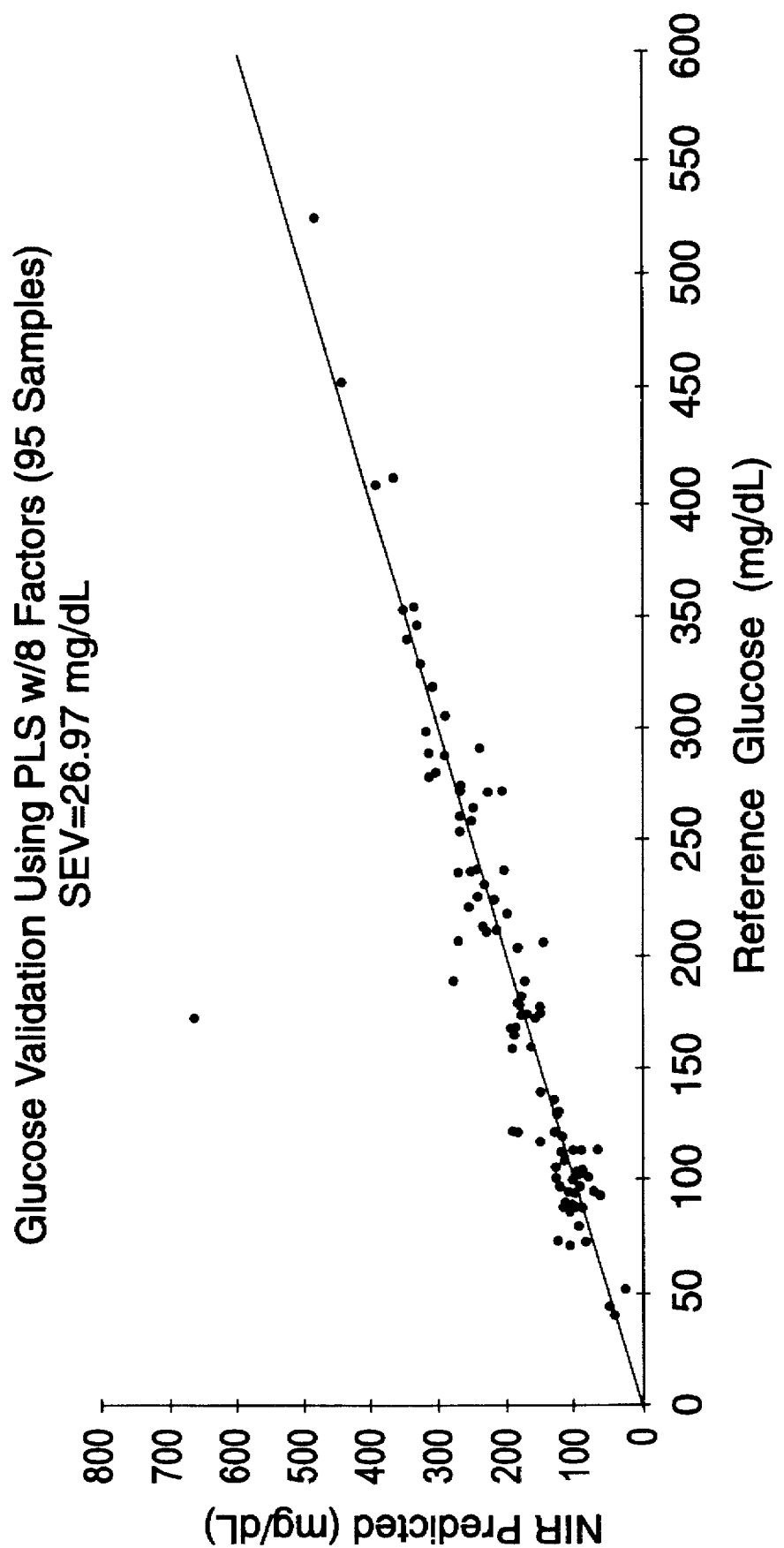
FIG. 15 is a scatter plot of predicted blood glucose concentrations from 95 samples using data derived from 2030 nm to 2398 nm, generated from a partial least squares model optimized with eight factors attaining a standard error of validation of 26.97 mg/dL versus actual blood glucose concentrations.

FIG. 16 sets forth a summary of 95 samples representing both major spectral regions examined using the method and apparatus of he present invention, and shows that blood glucose concentration predictions using the 95 and 100 sample data sets and the same spectral regions yielded very similar results. A slight reduction in prediction error to SEV of 26.97 mg/dL with respect to the 100 sample set depicted in FIG. 12 resulted for the 95 sample set depicted in FIG. 15 for the 2030 nm to 2398 nm region, with the difference representing approximately a 1% reduction in error. An F-test at the 95% confidence level did not find this a significant difference. Comparison of the partial least squares results from other spectral regions with various forms of data preprocessing yielded similar findings.

If a Mahalanobis distance threshold of 3.0 is used to determine outliers, a set of 89 samples results. Utilizing a partial least squares technique, leave-one-out validation on the set of 89 samples resulted in an SEV of 27.95 mg/dL, a slight increase over the 100 and 95 sample sets. It was separately determined that the six samples omitted in the 89 sample set with respect to the 95 sample set corresponded to samples having a high triglyceride concentration, a high total protein value, or both. The presence of the six outliers constituted an artifact of undersampling, that is, if a greater number of representative samples with high triglyceride or total protein concentrations were present in the original set of samples, samples having high triglyceride or total protein concentrations would be less likely to be flagged as outliers.

Sensitivity of outlier detection to triglyceride or any other analyte which affects spectral response may be advantageous, however. Spectral data may be partitioned such that samples with high triglycerides form a first calibration set while samples with low triglycerides form a second calibration set, so that new samples may be tested with the method and apparatus of the present invention to determine whether the first or second calibration set is representative of the new sample, thus allowing the selection of a prediction model determined from "similar" calibration spectra.

The present invention having been described in its preferred embodiments, it is clear that it is susceptible to numerous modifications and embodiments within the ability of those skilled in the art and without the exercise of the inventive faculty. As will be appreciated by those skilled in the art, the method and apparatus of the present invention encompasses alternative biological fluid analyte measurement techniques, including biological fluid analyte concentrations derived using light reflectance, light transmission, and other techniques used in conjunction with invasive, non-invasive, and in-vivo biological fluid analyte measurement techniques. In addition, measurements of biological fluid analytes may also include triglycerides, cholesterol, and serum proteins, with outlier detection using the method and apparatus of the present invention.

What is claimed is:

1. An improved method for forming a calibration model for use in determining concentration of an analyte of a biological fluid of a mammal, comprising the steps of:

collecting a set of calibration samples from a plurality of sources of the biological fluid;

generating near-infrared electromagnetic radiation having a plurality of wavelengths;

irradiating each of the calibration samples with the radiation so that a portion of the radiation at each of the wavelengths is transmitted through each of the calibration samples;

measuring intensity of the radiation transmitted through each of the calibration samples at each of the wavelengths thereby forming a set of calibration data;

processing the set of calibration data, including forming the set of calibration data into a n×p matrix defining a space, wherein n is the number of calibration samples and p is the number of wavelengths at which intensity of transmitted radiation is measured, forming a subspace of the space wherein sources of relatively greater variations within the set of calibration data are represented, projecting the set of calibration data into the subspace, determining a generalized distance within the subspace between each calibration sample and a centroid of a distribution formed by the set of calibration samples, identifying calibration outliers as those calibration samples having a generalized distance greater than a preselected magnitude, forming a reduced set of calibration samples from calibration samples remaining after removal of calibration outliers; and constructing a calibration model from the reduced set of calibration samples to predict concentration of the analyte in an unknown sample of the biological fluid.

2. The method as set forth in claim 1, wherein:

the step of forming a subspace includes decomposing the matrix by principal component analysis into an n×n dimensional score matrix and an n×p dimensional loading matrix, generating by principal component analysis a set of n eigenvectors and a set of n eigenvalues associated with the eigenvectors and arranged in order of decreasing magnitude, dividing the set of eigenvalues into a set of q larger, primary eigenvalues and a set of n–q smaller, error eigenvalues whereby the primary eigenvalues are associated with relatively more significant sources of variations within the set of calibration data and the error eigenvalues are associated with relatively less significant sources of variation within the set of calibration data, and generating the subspace as an n×q dimensioned principal component subspace from the space defined by the loading matrix; and the step of constructing a calibration model includes forming a regression coefficient matrix correlating the reduced set of calibration samples with the concentration of the analyte in the reduced set of calibration samples whereby the regression coefficient matrix may be used to predict concentration of the analyte in an unknown sample of the biological fluid given the intensity of the radiation transmitted therethrough at each of the wavelengths.

3. The method as set forth in claims 1 or 2, wherein each of the generalized distances is a Mahalanobis distance determined from the following relationship:

$$MD_i = [(x_i - \bar{x}) S^{-1} (x_i - \bar{x})^t]^{1/2}$$

wherein $MD_i$ is the Mahalanobis distance between an $i^{th}$ calibration sample $x_i$ and the centroid $\bar{x}$ of the set of calibration samples, $S^{-1}$ is the inverted variance-covariance matrix of the set of calibration data, and $(x_i - \bar{x})^t$ is the transpose of $(x_i - \bar{x})$.

4. The method as set forth in claims 1 or 2, wherein each generalized distance is a Robust distance determined using an algorithm selected from the group consisting of minimum volume ellipsoid estimator and projection algorithm.

5. The method as set forth in claims 1 or 2, further including the step of pretreating the set of calibration data to remove and compensate for spectral artifacts prior to the step of processing the set of calibration data.

6. The method as set forth in claim 5, wherein the step of pretreating the set of calibration data is performed using an algorithm selected from the group consisting of nth order derivatives, multiplicative scatter correction, n-point smoothing, mean centering, variance scaling, and ratiometric method.

7. The method as set forth in claims 1 or 2, further including the steps of:

forming a ratio of the number of calibration outliers to the number of calibration samples;

determining whether the ratio is greater than a preselected ratio; and pretreating the set of calibration data to remove and compensate for spectral artifacts prior to the step of processing the set of calibration data if the ratio exceeds the preselected ratio.

8. The method as set forth in claims 1 or 2, wherein the step of identifying calibration outliers includes selecting the magnitude by determining a probability that each member of the set of calibration samples belongs to a class defined by a preselected probability distribution function whereby calibration outliers are identified as calibration samples whose class membership may be rejected at a confidence level greater than a preselected level.

9. The method as set forth in claim 8, wherein the probability distribution function is formed using an algorithm selected from the group consisting of chi-squared distribution function evaluation and Hotelling's T-statistic evaluation.

10. The method as set forth in claim 8, wherein the preselected level is in the range of approximately 3 to 5 standard deviations as defined by the probability distribution function.

11. An improved method for determining concentration of an analyte of a biological fluid of a mammal, comprising the steps of:

collecting a set of calibration samples from a plurality of sources of the biological fluid and an unknown sample from an unknown source of the biological fluid;

generating near-infrared electromagnetic radiation having a plurality of wavelengths;

irradiating each of the calibration samples and the unknown sample with the radiation so that a portion of the radiation at each of the wavelengths is transmitted through each of the calibration samples and the unknown sample;

measuring intensity of the radiation transmitted through each of the calibration samples at each of the wavelengths thereby forming a set of calibration data and through the unknown sample at each of the wavelengths thereby forming a set of sample data;

processing the set of calibration data, including forming the set of calibration data into a n×p matrix defining a space, wherein n is the number of calibration samples and p is the number of wavelengths at which intensity of transmitted radiation is measured, forming a subspace of the space wherein sources of relatively greater variations within the set of calibration data are represented, projecting the set of calibration data into the subspace, determining a generalized distance within the subspace between each calibration sample and a centroid of a distribution formed by the set of calibration samples, identifying calibration outliers as those calibration samples having a generalized distance greater than a preselected magnitude, forming a reduced set of calibration samples from calibration samples remaining after removal of calibration outliers;

constructing a calibration model from the reduced set of calibration samples to predict concentration of the analyte in the unknown sample; and applying the calibration model to the set of sample data including projecting the set of sample data into the space defined by the model, determining a generalized distance for the unknown sample according to the model, identifying the unknown sample as a sample outlier provided the generalized distance of the unknown sample is greater than the preselected magnitude, and predicting concentration of the analyte in the unknown sample according to the model provided the generalized distance of the unknown sample is not greater than the preselected magnitude.

12. The method as set forth in claim 11, wherein:

the step of forming a subspace includes decomposing the matrix by principal component analysis into an n×n dimensional score matrix and an n×p dimensional loading matrix, generating by principal component analysis a set of n eigenvectors and a set of n eigenvalues associated with the eigenvectors and arranged in order of decreasing magnitude, dividing the set of eigenvalues into a set of q larger, primary eigenvalues and a set of n−q smaller, error eigenvalues whereby the primary eigenvalues are associated with relatively more significant sources of variations within the set of calibration data and the error eigenvalues are associated with relatively less significant sources of variation within the set of calibration data, and generating the subspace as an n×q dimensioned principal component subspace from the space defined by the loading matrix; and the step of constructing a calibration model includes forming a regression coefficient matrix correlating the reduced set of calibration samples with the concentration of the analyte in the reduced set of calibration samples whereby the regression coefficient matrix may be used to predict concentration of the analyte in an unknown sample of the biological fluid given the intensity of the radiation transmitted therethrough at each of the wavelengths.

13. The method as set forth in claims 11 or 12, wherein each of the generalized distances of the set of calibration samples is a Mahalanobis distance determined from the following relationship:

$$MD_i = [(x_i - \bar{x}) S^{-1} (x_i - \bar{x})']^{1/2}$$

wherein $MD_i$ is the Mahalanobis distance between an $i^{th}$ calibration sample $x_i$ and the centroid $\bar{x}$ of the set of calibration samples, $S^{-1}$ is the inverted variance-covariance matrix of the set of calibration data, and $(x_i - \bar{x})'$ is the transpose of $(x_i - \bar{x})$, and wherein the generalized distance of the unknown sample according to the model is a Mahalanobis distance determined from the following relationship:

$$MD_{sample} = [(x_{sample} - \bar{x}_{model}) S^{-1}(x_{sample} - \bar{x}_{model})']^{1/2}$$

wherein $MD_{sample}$ is the Mahalanobis distance between the unknown sample and the centroid $\bar{x}_{model}$ of the model $S^{-1}_{model}$ is the inverted variance-covariance matrix of the model, and $(x_{sample} - \bar{x}_{model})'$ is the transpose of $(x_{sample} - \bar{x}_{model})$.

14. The method as set forth in claims 11 or 12, wherein each of the generalized distances of the set of calibration data is a Robust distance determined using an algorithm selected from the group consisting of minimum volume ellipsoid estimator and projection algorithm.

15. The method as set forth in claims 11 or 12, further including the steps of:

forming a ratio of the number of calibration outliers to the number of calibration samples;

determining whether the ratio is greater than a preselected ratio;

pretreating the set of calibration data to remove and compensate for spectral artifacts prior to the step of processing the set of calibration data if the ratio exceeds the preselected ratio; and pretreating the sample data to remove and compensate for spectral artifacts prior to the step of applying the calibration model to the sample data if the ratio exceeds the preselected ratio.

16. The method as set forth in claims 11 or 12, further including the steps of:

pretreating the set of calibration data to remove and compensate for spectral artifacts prior to the step of processing the set of calibration data; and pretreating the sample data to remove and compensate for spectral artifacts prior to the step of applying the calibration model to the sample data.

17. The method as set forth in claim 16, wherein the steps of pretreating the set of sample data and pretreating the set of calibration data are each performed using an algorithm selected from the group consisting of nth order derivatives, multiplicative scatter correction, n-point smoothing, mean centering, variance scaling, and ratiometric method.

18. The method as set forth in claims 11 or 12, wherein the step of identifying calibration outliers includes selecting the magnitude by determining a probability that each member of the set of calibration samples belongs to a class defined by a preselected probability distribution function whereby calibration outliers are identified as calibration samples whose class membership may be rejected at a confidence level greater than a preselected level, and wherein the step of identifying a sample outlier includes determining whether probability of class membership of the unknown sample may be rejected at a confidence level greater than the preselected level, according to the model.

19. The method as set forth in claim 18, wherein the probability distribution function is formed using an algorithm selected from the group consisting of chi-squared distribution function evaluation and Hotelling's T-statistic evaluation.

20. The method as set forth in claim 18, wherein the preselected level is in the range of approximately 3 to 5 standard deviations as defined by the probability distribution function.

21. The method as set forth in claim 12, wherein the unknown sample and each of the calibration samples includes a second analyte having concentration within a preselected range.

22. The method as set forth in claim 21, wherein the second analyte is triglycerides.

23. The method as set forth in claim 22, wherein the second analyte is total protein.

24. The method as set forth in claims 1, 2, 11 or 12, wherein the step of constructing a calibration model includes removing redundant data from data corresponding to the reduced set of calibration samples.

25. The method as set forth in claims 1, 2, 11 or 12, wherein the step of constructing a calibration model is performed using an algorithm selected from the group consisting of principal component regression, partial least squares, multiple linear regression, and artificial neural networks.

26. The method as set forth in claims 1, 2, 11 or 12, wherein the step of constructing a calibration model is performed using an algorithm selected from the group consisting of principal component regression, partial least squares, and multiple linear regression, and includes selecting an optimal number of score vectors to use in the calibration model whereby redundant data may be removed from data corresponding to the reduced set of calibration samples.

27. The method as set forth in claim 26 wherein the step of selecting the optimal number of score vectors includes:

constructing n preliminary calibration models, each preliminary calibration model using a different number of score vectors selected from a range of 1 through n;

determining a standard error of prediction for each of the preliminary calibration models; and comparing the standard error of prediction for the preliminary models to determine the optimal number of score vectors.

28. The method as set forth in claim 27 wherein comparing the standard error of prediction is performed using an algorithm selected from the group consisting of F-test and local minimum determination.

29. The method as set forth in claims 2 or 12, wherein the step of dividing the set of eigenvalues includes determining the number of primary eigenvalues q by an iterative method which compares variance of the $q^{th}$ eigenvalue to the variance of the pooled error eigenvalues using an F-test.

30. The method as set forth in claim 29, wherein the step of determining the number of primary eigenvalues q includes weighing the eigenvalues by an amount proportional to information explained by associated eigenvectors to produce a set of reduced eigenvalues.

31. Apparatus for determining concentration of an analyte in an unknown sample of a biological fluid of a mammal comprising:

a positioner unit capable of sequentially positioning the unknown sample and each of a set of calibration samples of the biological fluid collected from a plurality of sources;

a radiation emitter capable of emitting near-infrared electromagnetic radiation at a preselected plurality of wavelengths, said radiation emitter positioned to sequentially direct radiation of each of the wavelengths into and partially through each of the calibration samples and the unknown sample;

a near-infrared electromagnetic radiation detector disposed to sequentially receive and measure intensity of the radiation transmitted through each of the calibration samples at each of the wavelengths to form a set of calibration data and through the unknown sample to form a set of sample data; and a computer connected to said detector and having a general purpose microprocessor configured with computer program code to form the set of calibration data into a matrix defining a space, form a subspace of the space wherein sources of relatively greater variations within the set of calibration data are represented, project the set of calibration data into the subspace, determine a generalized distance within the subspace between each calibration sample and a centroid defined by a distribution formed by the set of calibration samples, identify calibration outliers as those calibration samples having a generalized distance greater than a preselected magnitude, form a reduced set of calibration samples from calibration samples remaining after removal of calibration outliers, construct a calibration model from the reduced set of calibration samples to predict concentration of the analyte in the unknown sample, project the set of sample data into a space defined by the model, determine a generalized distance for the unknown sample according to the model, identify the unknown sample as a sample outlier provided the generalized distance of the unknown sample is greater than the preselected magnitude, and predict concentration of the analyte in the unknown sample according to the model provided the generalized distance of the unknown sample is not greater than the preselected magnitude.

32. The apparatus of claim 31, wherein said positioner unit comprises:

a flowcell having an input orifice and an output orifice; and a pump disposed in fluid connection between said input orifice and said output orifice whereby each of the set of calibration samples and the unknown sample may be sequentially circulated through said flowcell.

33. The apparatus of claim 31, further comprising a temperature controller capable of controlling temperature of said positioner unit and said detector.

34. The apparatus of claim 31, wherein each of the generalized distances is a Mahalanobis distance determined from the following relationship:

$$MD_i = [(x_i - \bar{x}) S^{-1} (x_i - \bar{x})']^{1/2}$$

wherein $MD_i$ is the Mahalanobis distance between an $i^{th}$ calibration sample and the centroid $\bar{x}$ of the set of calibration samples, $S^{-1}$ is the inverted variance-covariance matrix of the set of calibration data, and $(x_i - \bar{x})'$ is the transpose of $(x_i - \bar{x})$.

35. The apparatus of claim 31, wherein each generalized distance is a Robust distance determined using an algorithm selected from the group consisting of minimum volume ellipsoid estimator and projection algorithm.

36. The apparatus of claim 31, further comprising a noise reducer coupled to said radiation emitter and said detector, and capable of reducing noise in measurements of intensity of that portion of the radiation transmitted through each of the calibration samples and the unknown sample.

37. Apparatus for determining concentration of an analyte in an unknown sample of a biological fluid of a mammal comprising:

a positioner unit capable of sequentially positioning the unknown sample and each of a set of calibration samples of the biological fluid collected from a plurality of sources, including a flowcell having an input orifice and an output orifice, and a pump disposed in fluid connection between said input orifice and said output orifice whereby each of the set of calibration samples and the unknown sample may be sequentially circulated through said flowcell;

a radiation emitter capable of emitting near-infrared electromagnetic radiation at a preselected plurality of wavelengths, said radiation emitter positioned to sequentially direct the radiation of each of the wavelengths into and partially through each of the calibration samples and the unknown sample;

a near-infrared electromagnetic radiation detector disposed to sequentially receive and measure intensity of the radiation transmitted through each of the calibration samples at each of the wavelengths to form a set of calibration data and through the unknown sample to form a set of sample data;

a temperature controller capable of controlling temperature of said positioner unit and said detector;

a noise reducer coupled to said radiation emitter and said detector, and capable of reducing noise in measurements of intensity of that portion of the radiation transmitted through each of the calibration samples and the unknown sample; and a computer connected to said detector and having a general purpose microprocessor configured with computer program code to form the set of calibration data into a matrix defining a space, form a subspace of the space wherein sources of relatively greater variations within the set of calibration data are represented, project the set of calibration data into the subspace, determine a generalized distance within the subspace between each calibration sample and a centroid defined by a distribution formed by the set of calibration samples, identify calibration outliers as those calibration samples having a generalized distance greater than a preselected magnitude, form a reduced set of calibration samples from calibration samples remaining after removal of calibration outliers, construct a calibration model from the reduced set of calibration samples to predict concentration of the analyte in the unknown sample, project the set of sample data into a space defined by the model, determine a generalized distance for the unknown sample according to the model, identify the unknown sample as a sample outlier provided the generalized distance of the unknown sample is greater than the preselected magnitude, and predict concentration of the analyte in the unknown sample according to the model provided the generalized distance of the unknown sample is not greater than the preselected magnitude.

38. The apparatus of claim 37, wherein each of the generalized distances is a Mahalanobis distance determined from the following relationship:

$$MD_i = [(x_i - \bar{x}) S^{-1} (x_i - \bar{x})^t]^{1/2}$$

wherein $MD_i$ is the Mahalanobis distance between an $i^{th}$ calibration sample and the centroid $\bar{x}$ of the set of calibration samples, $S^{-1}$ is the inverted variance-covariance matrix of the set of calibration data, and $(x_i - \bar{x})^t$ is the transpose of $(x_i - \bar{x})$.

39. The apparatus of claim 37, wherein each generalized distance is a Robust distance determined using an algorithm selected from the group consisting of minimum volume ellipsoid estimator and projection algorithm.

40. The apparatus of claims 36, 38, or 39, wherein:

said radiation emitter includes a relatively broad bandwidth near-infrared electromagnetic radiation source and a monochrometer disposed between said source and said positioner unit; and said noise reducer includes a chopper disposed between said source and said monochrometer whereby radiation from said source may be alternatively blocked from transmission to said monochrometer, and a synchronizer operably connected to said chopper and said detector whereby signals produced in said detector when radiation from said source is blocked by said chopper may be subtracted from signals produced in said detector when radiation from said source is not blocked by said chopper.

41. The apparatus of claims 36, 38, or 39, wherein:

said radiation emitter includes a relatively broad bandwidth near-infrared electromagnetic radiation source and a filter wheel disposed between said source and said positioner unit; and said noise reducer includes a chopper disposed between said source and said monochrometer whereby radiation from said source may be alternatively blocked from transmission to said monochrometer, and a synchronizer operably connected to said chopper and said detector whereby signals produced in said detector when radiation from said source is blocked by said chopper may be subtracted from signals produced in said detector when radiation from said source is not blocked by said chopper.

42. The apparatus of claims 36, 38, or 39, wherein:

said radiation emitter includes a plurality of relatively narrow bandwidth near-infrared electromagnetic radiation sources connected to said computer whereby said sources may be activated in a preselected sequential order; and said noise reducer includes a pulse driver operably connected to each of said sources and said detector whereby signals produced in said detector when radiation from set of sources is not pulsed by said driver may be subtracted from signals produced in said detector when radiation from said sources is pulsed by said driver.

* * * * *

UNITED STATES PATENT AND TRADEMARK OFFICE
CERTIFICATE OF CORRECTION

PATENT NO. : 5,606,164
DATED : February 25, 1997
INVENTOR(S) : John F. Price and James R. Long It is certified that error appears in the above-identified patent and that said Letters Patent is hereby corrected as shown below:

On the bibiography page, please insert the following information:
--Related U.S. Application Data
[60] Provisional application No. 60/001,950, Aug. 7, 1995, now abandoned--

Signed and Sealed this

Twenty-first Day of October 1997

Attest:

BRUCE LEHMAN

*Attesting Officer*  *Commissioner of Patents and Trademarks*